(12) United States Patent
Bissinger et al.

(10) Patent No.: US 8,003,711 B2
(45) Date of Patent: *Aug. 23, 2011

(54) DENTAL COMPOSITION CONTAINING SI-H FUNCTIONAL CARBOSILANE COMPONENTS

(75) Inventors: Peter Bissinger, Diessen (DE); Adrian S. Eckert, Munich (DE); Reinhold Hecht, Kaufering (DE); Uwe H. Hoheisel, Turkenfeld (DE)

(73) Assignee: 3M Innovative Properties Company, Saint Paul, MN (US)

( * ) Notice: Subject to any disclaimer, the term of this patent is extended or adjusted under 35 U.S.C. 154(b) by 1033 days.

This patent is subject to a terminal disclaimer.

(21) Appl. No.: 11/572,056

(22) PCT Filed: Jul. 14, 2004

(86) PCT No.: PCT/EP2004/007783
§ 371 (c)(1),
(2), (4) Date: Jan. 12, 2007

(87) PCT Pub. No.: WO2006/005366
PCT Pub. Date: Jan. 19, 2006

(65) Prior Publication Data
US 2007/0238803 A1 Oct. 11, 2007

(51) Int. Cl.
*A61C 5/00* (2006.01)
*A61K 6/08* (2006.01)
*C08G 77/06* (2006.01)

(52) U.S. Cl. .............. 523/116; 528/12; 528/25; 528/43; 433/215; 433/228.1

(58) Field of Classification Search .................. 523/116; 528/12, 25, 43
See application file for complete search history.

(56) References Cited

U.S. PATENT DOCUMENTS

| | | | |
|---|---|---|---|
| 3,220,972 A * | 11/1965 | Lamoreaux | 528/15 |
| 3,715,334 A | 2/1973 | Karstedt | |
| 3,775,352 A | 11/1973 | Leonard | |
| 3,814,730 A | 6/1974 | Karstedt | |
| 3,927,116 A | 12/1975 | Rick et al. | |
| 3,933,880 A | 1/1976 | Bergstrom et al. | |
| 3,971,754 A | 7/1976 | Jurecic | |
| 4,391,590 A | 7/1983 | Dougherty | |
| 4,704,438 A | 11/1987 | Niwa et al. | |
| 4,767,798 A | 8/1988 | Gasser et al. | |
| 4,788,268 A | 11/1988 | Lau et al. | |
| 5,145,886 A | 9/1992 | Oxman et al. | |
| 5,165,890 A | 11/1992 | Discko | |
| 5,233,006 A | 8/1993 | Wolter et al. | |
| 5,322,440 A | 6/1994 | Steele | |
| 5,367,001 A | 11/1994 | Itoh et al. | |
| 5,583,178 A * | 12/1996 | Oxman et al. | 524/862 |
| 5,691,433 A | 11/1997 | Kotani et al. | |
| 6,046,250 A | 4/2000 | Boardman et al. | |
| 6,245,828 B1 | 6/2001 | Weinmann et al. | |
| 6,335,413 B1 | 1/2002 | Zech et al. | |
| 6,376,569 B1 | 4/2002 | Oxman et al. | |
| 6,566,413 B1 | 5/2003 | Weinmann et al. | |
| 6,596,821 B1 | 7/2003 | Katsoulis et al. | |
| 6,624,236 B1 | 9/2003 | Bissinger et al. | |
| 6,653,375 B2 | 11/2003 | Moszner et al. | |
| 6,852,822 B1 | 2/2005 | Bissingner et al. | |
| 7,576,144 B2 | 8/2009 | Lewandowski et al. | |
| 2002/0082315 A1 | 6/2002 | Moszner et al. | |
| 2003/0035899 A1 | 2/2003 | Klettke et al. | |
| 2003/0166816 A1 | 9/2003 | Bissinger et al. | |
| 2004/0110863 A1 | 6/2004 | Zech et al. | |

FOREIGN PATENT DOCUMENTS

| | | | |
|---|---|---|---|
| EP | 0 238 025 A2 | | 9/1987 |
| EP | 0 451 709 A2 | | 10/1991 |
| EP | 1 368 402 A1 | | 8/2004 |
| EP | 1 512 724 A1 | | 9/2005 |
| JP | 10152615 | | 9/1998 |
| WO | WO 86/01219 | * | 2/1986 |
| WO | WO 00/38619 | | 7/2000 |
| WO | WO 01/07444 A1 | | 2/2001 |
| WO | WO 01/92271 A1 | | 12/2001 |
| WO | WO 01/95862 A1 | | 12/2001 |
| WO | WO 02/066535 A1 | | 8/2002 |
| WO | WO 2006/005363 A1 | | 1/2006 |
| WO | WO 2006/005366 A1 | | 1/2006 |
| WO | WO 2006/005368 A1 | | 1/2006 |

OTHER PUBLICATIONS

Beck, H., N., Chaffee, R., G., Phenenyl Silicon Compounds, J. Chem. Eng. Data 1963, 8(3), 453-454.
Houben-Weyl, Methoden d. Organ. Chemie, vol. VI/3, p57 (1st preparation example) or p. 56 (1st prep. example), Georg Thieme Verlag, Stuttgart, 1965, 4. edition.
Houben-Weyl, Methoden d. Organ. Chemie, vol. XIII/2a, p47ff., Georg Thieme Verlag, Stuttgart, 1973, 4. edition.
Marciniec, B., Comprehensive Handbook on Hydosilylation, Pergamon press, Oxford, 1992.
Marciniec, B., Comprehensive Handbook on Hydrosilylation, p8ff, Pergamon Press, Oxford, 1992.
Marciniec, B., Comprehensive Handbook on Hydrosilylation,. p107ff., Pergamon Press, Oxford, 1992. Tarbell, D., S., Wilson, J., W., The Rearrangement of 4-Crotyloxy-3,5-Dichlorobenzoic Acid, J.Am.Chem.Soc. 1942, 64(5), 1066-1070.
DIN EN ISO 4049, 2001.
DIN EN ISO 9917-1, 2004.
DIN EN ISO 9917-2, 1999.
International Preliminary Report on Patentability and Written Opinion for PCT/EP2004/007783; 6 pgs, 2005.
European Office Communication dated Feb. 2, 2010, 4 pgs.

* cited by examiner

*Primary Examiner* — Tae H Yoon
(74) *Attorney, Agent, or Firm* — Pamela L. Stewart

(57) ABSTRACT

The invention relates to a dental composition comprising a) carbosilane containing component (A) comprising at least 1 Si-Aryl bond, at least 1 silicon atom, at least 2 Si—H functional moieties, no Si-Oxygen bond, b) unsaturated component (131), and/or epoxy component (132), c) initiator (C), d) optionally filler (D) and e) optionally component (E) selected from modifiers, dyes, pigments, thixotropic agents, flow improvers, polymeric thickeners, surfactants, odorous substances, diluting agent(s) and flavorings.

21 Claims, No Drawings

DENTAL COMPOSITION CONTAINING SI-H FUNCTIONAL CARBOSILANE COMPONENTS

CROSS REFERENCE TO RELATED APPLICATIONS

This application is a national stage filing under 35 U.S.C. 371 of PCT/EP2004/007783 filed Jul. 14, 2004.

The invention relates to a curable dental composition containing a Si—H functional carbosilane component. The composition has improved properties and can be used e.g. as a dental filling material.

The dental filling materials on the market can generally be divided into composites, resin modified glass ionomer cements and glass ionomer cements (GIZ). The composites cure usually via a light induced radical polymerisation of unsaturated components, especially (meth)acrylates. The glass ionomer cements cure by a cement setting reaction, whereas the resin modified glass ionomer cements cure using both mechanisms.

Of special interest are the dental composites, the curing of which results in a very hard material compared to the glass ionomer cements, which are especially useful for filling teeth cavities. However, a well-known disadvantage of the dental composites on the market is that the compositions shrink on curing. A further drawback is that some of the components of the dental composite materials are not hydrolytically very stable and/or are comparably hydrophilic, and thus undesirable substances can emerge from the cured composition over the years.

Attempts were made to solve the above-mentioned problems.

In this respect U.S. Pat. No. 6,653,375 B2 describes urethane di(meth)acrylate derivatives of 1,3-bis(1-isocyanato-1-1methylethyl)benzene. It is stated that the monomers have a refractive index compatible with that of customary dental filling materials, do not tend towards discolorations and can replace bis-GMA in dental materials without impairing the mechanical properties of the materials.

U.S. Pat. No. 6,624,236 B1 is directed to cyclosiloxane-based crosslinkable monomers, production thereof and use thereof in polymerisable materials, in particular to polysiloxanes from sol-gel-condensable cyclosiloxane (meth)acrylates as well as resinous compositions.

U.S. Pat. No. 6,566,413 B1 relates to polymerisable materials based on hardenable siloxane compounds useful for dental compositions. It is described that the siiloxane compounds used display a low viscosity, permit a high filler uptake and lead to compositions with a low polymerisation shrinkage.

In WO 01/92271 A1 prepolymeric (meth)acrylates with polycyclic or aromatic segments are described useful for the preparation of dental materials. It is said that the siloxane monomers have a high molecular weight (e.g. over 600 g/mol), have a high (meth)acrylate functionality and a low visclosity.

WO 2001095862 A1 refers to a low shrinking polymerisable dental material including a mixture of di- or poly(meth)acrylate, an alkoxylated bisphenol dimethacrylate, a polymerisable monomer, a polymerisation initiator and/or sensitizer, a stabilizer and a filler. It is mentioned that the volumetric shrinkage during polymerisation is less than 2 Vol-%.

EP 0 451 709 A2 discloses silanes of a certain formula which can comprise groups containing (meth)acrylate moieties. It is stated that the silanes can be used as such or as additives for coating compositions, bulk materials, adhesives and compositions for injection moulding.

The solutions described above however are not completely satisfying.

Therefore, there is a need for alternatives. There is especially a need for alternative materials with improved properties.

It is thus an object of the present invention to alleviate one or more of the problems mentioned above.

It is also an object of the present invention to provide an esthetical composition if used in the dental field.

It is another object of the present invention to provide a lipophilic composition.

It is a further object of the present invention to provide a composition with improved properties, especially a composition which enables one to provide a composition having a low shrinkage value.

It has been found that one or more of the above mentioned objects can be achieved by providing a composition as described in the text below.

Surprisingly, it has been found that using carbosilane compounds comprising Si—H functional groups, and not containing carbosiloxane structures, enables one to provide curable dental compositions with improved properties.

Thus, the present invention relates to a dental composition comprising
  a) carbosilane containing component (A) comprising
    at least 1 Si-Aryl bond,
    at least 1 silicon atom,
    at least 2 Si—H functional moieties, wherein one silicon atom can bear more than one H atom;
    no Si-Oxygen bond,
  b) unsaturated component (B1), and/or epoxy component (B2),
  c) initiator (C),
  d) optionally filler (D),
  e) optionally component (E) selected from modifiers, dyes, pigments, thixotropic agents, flow improvers, polymeric thickeners, surfactants, odorous substances, diluting agent(s) and flavourings.

The invention also relates to a method of producing the composition as described in the text below.

Additionally, the invention relates to a method of using the composition as described in the text below.

Carbosilane containing component (A) can be used alone or in a mixture with other Si—H functional compounds as reactive compounds in dental materials that may also contain other reactive and/or unreactive components, if needed.

This invention offers a way to provide dental composition with improved properties. Carbosilane containing component (A) might show a comparably high refractive index together with a comparably low viscosity so that the dental compositions provided might have an excellent opacity and thus can be highly esthetic. Moreover, the compositions might show comparably low shrinkage as well as low uptake of water and/or water soluble dyes (e.g. from coffee, tea, red wine) after curing compared to other dental compositions on the market.

The terms "comprise" and "contain" within the meaning of the invention introduce a non exhaustive list of features. Likewise, the word "one" or "a" is to be understood in the sense of "at least one".

The term "dental composition" according to the invention is a curable composition to be used in the dental field for different purposes, usually in small amounts of a few grams.

The term "unsaturated component" according to the invention is a substance or mixture of substances each containing at least 1 olefinic group within the molecule.

The term "epoxy component" according to the invention is a substance or mixture of substances each containing at least 1 epoxy group within the molecule.

The term "initiator" according to the invention is a substance or mixture of substances capable of starting a curing reaction, preferably a hydrosilylation curing reaction and/or a metal induced cationic ring opening polymerization reaction of epoxies.

The term "Si—H functional moiety" according to the invention refers to a moiety which is polymerisable, especially via hydrosilylation reaction and/or a metal induced cationic ring opening polymerization reaction of epoxies, comprising preferably a Si—H functional group.

The term "aryl" according to the invention refers to an aromatic moiety such as phenyl, naphthyl. Besides an attached Si-Atom, the aryl moiety can bear 1 or 2 substituents, preferably alkyl and/or aryl ether groups (e.g. $C_{1-8}$ alkyl, $C_{2-10}$ alkenyl, $C_{3-6}$ cycloalkyl, $C_{4-6}$ cycloalkenyl, $C_{6-10}$ aryl).

Carbosilane containing component (A) can be synthesized e.g. via Grignard reaction (cf. Houben-Weyl, Methoden der Organischen Chemie, volume XIII/2a, p47ff., Georg Thieme Verlag, Stuttgart, 1973, 4. edition) or e.g. via hydrosilylation reaction (cf. Marciniec, B., Comprehensive Handbook on Hydrosilylation, Pergamon Press, Oxford, 1992) according to scheme (I) by reacting (poly)organometallic functional component (i) with silicon containing component (ii).

The Grignard reaction is a nucleophilic substitution reaction where a metal organic compound (i) is substituting a leaving group LG of e.g. silicon containing compound (ii) forming a new Si—C single bond and yielding silicon containing compound (iii):

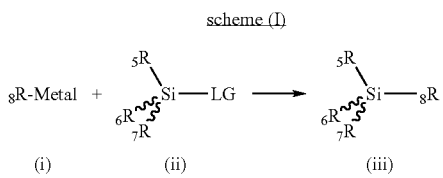

scheme (I)

wherein $R_5$, $R_6$, $R_7$, $R_8$=H or (cyclo)aliphatic or aromatic or (cyclo)aliphatic aromatic or aromatic (cyclo)aliphatic moiety wherein C and/or H atoms can be substituted by e.g. O, Br, Cl, and Si atoms and that can also contain olefinic groups.

A metal organic compound (i) can be used according to scheme (I) as described e.g. for siloxane based compounds in U.S. Pat. No. 4,788,268 (preparation examples 1, 2, 4, 5, 6, and 7 in columns 6-17) or can be used as an intermediate of an in situ Grignard reaction starting from halogenated precursors via an in situ Grignard reaction as e.g. described for other carbosilane compounds like 1,3,5-Tris(dimethylsilyl)benzene and 2,4,6-Tris(dimethylsilyl)anisole by Beck, H., N., Chaffee, R., G., J. Chem. Eng. Data 1963, 8(3), 453-454.

(Poly)halogenated precursors like 1,3,5-Tribromo-benzene and 2,4,6-Tribromo-anisole are commercially available or can be synthesized like 1,5-Bis(3,5-dichloro-phenoxy)-pentane or 2,2-Bis[3,5-dibromo-4-(3-methylbutyloxy)-phenyl]-propane as described e.g. for similar aryl alkyl ether compounds like Allyl-phenyl-ether or But-2-enyl-(2-methoxy-phenyl)-ether in Houben-Weyl, Methoden der Organischen Chemie, volume VI/3, p57 (first prepartion example) or p56 (first preparation example), Georg Thieme Verlag, Stuttgart, 1965, 4. edition or like Allyl-(2-chloro-phenyl)-ether as e.g. described by Tarbell, D., S., Wilson, J., W., J. Am. Chem. Soc. 1942, 64(5), 1066-1070.

Silicon containing components (ii) like Chloro-dimethyl-silane, Chloro-methyl-phenyl-silane, Chloro-diphenyl-silane, Chloro-methyl-silane, Chloro-phenyl-silane, or Chloro-silane are commercially available.

Carbosilane containing component (A) of the invention can also be obtained via hydrosilylation reaction according to scheme (II) by reacting a poly Si—H functional carbosilane component (iv) with a non-silicon containing diolefinic precursor (v) using e.g. common noble metal compounds as catalyst as described e.g. in Marciniec, B., Comprehensive Handbook on Hydrosilylation, p107ff., Pergamon Press, Oxford, 1992 or e.g. for siloxane based compounds in U.S. Pat. No. 6,245,828 (first step of syntheses of preparation examples 2-3 in column 19).

The hydrosilylation reaction is an addition reaction where a Si—H functional compound (iv) is added to an olefinic functional compound (v) in the presence of a catalyst as indicated in scheme (II) forming a new Si—C single bond and yielding a silicon containing compound (vi):

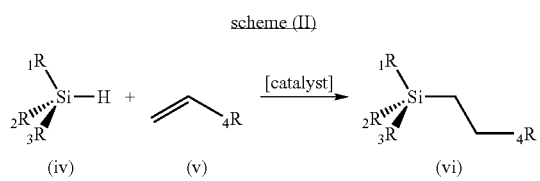

scheme (II)

wherein $R_1$, $R_2$, $R_3$, $R_4$=H or (cyclo)aliphatic or aromatic or (cyclo)aliphatic aromatic or aromatic (cyclo)aliphatic moiety wherein C and/or H atoms can also be substituted by e.g. O, Br, Cl, and Si atoms and that can also contain functionalities like olefinic groups.

Si—H functional carbosilane components (iv) like 1,3,5-Tris(dimethylsilyl)benzene and 2,4,6-Tris(dimethylsilyl)anisole can be synthesized via in situ Grignard reaction as e.g. described by Beck, H., N., Chaffee, R., G., J. Chem. Eng. Data 1963, 8(3), 453-454.

Non-silicon containing diolefinic precursors (v) like BisPhenol A diallylether or Tetrabromo BisPhenol A diallylether are commercially available or can be synthesized like 2,2-Bis[3,5-dibromo-4-(4-pentenyloxy)-phenyl]-propane as described e.g. for aryl alkyl ether compounds like Allyl-phenyl-ether or But-2-enyl-(2-methoxy-phenyl)-ether in Houben-Weyl, Methoden der Organischen Chemie, volume VI/3, p57 (first preparation example) or p56 (first preparation example), Georg Thieme Verlag, Stuttgart, 1965, 4. edition or like e.g. Allyl-(2-chloro-phenyl)-ether as e.g. described by Tarbell, D., S., Wilson, J., W., J. Am. Chem. Soc. 1942, 64(5), 1066-1070.

Carbosilane containing component (A) of the inventive composition comprises preferably the following chemical moieties:

Si-Aryl bonds: at least 1, 2, 3 or 4;

silicon atoms: at least 1, 2, 3, 4, 5, or 6, preferably 2 to 4;

Si—H functional moieties: at least 2, 3, 4, 5, or 6, preferably 2 to 4;
Si-Oxygen bonds: none;
aromatic moieties: at least 1, 2, 3 or 4;
optionally a bisphenol derived spacer moiety.

The amount of carbosilane containing component (A) can be as low as about 1 wt.-%, or as low as about 3 wt.-%, or as low as about 10 wt.-% with respect to the cured composition The amount of carbosilane containing component (A) can be as high as about 90 wt.-%, or as high as about 65 wt.-%, or as high as about 30 wt.-% with respect to the cured composition.

The amount of unsaturated component (B1) can be as low as about 1 wt.-%, or as low as about 3 wt.-%, or as low as about 10 wt.-% with respect to the cured composition.

The amount of unsaturated component (B1) can be as high as about 90 wt.-%, or as high as about 65 wt.-%, or as high as about 30 wt.-% with respect to the cured composition.

The amount of epoxy component (B2) can be as low as about 1 wt.-%, or as low as about 3 wt.-%, or as low as about 10 wt.-% with respect to the cured composition.

The amount of epoxy component (B2) can be as high as about 90 wt.-%, or as high as about 65 wt.-%, or as high as about 30 wt.-% with respect to the cured composition.

The amount of initiator (C) can be as low as about 0.00005 wt.-%, or as low as about 0.0002 wt.-%, or as low as about 0.002 wt.-% with respect to the cured composition and calculated as elemental metal and related to the overall weight of the material present regarding components (A) to (E).

The amount of initiator (C) can be as high as about 1.0 wt.-%, or as high as about 0.5 wt.-%, or as high as about 0.1 wt.-% with respect to the cured composition and calculated as elemental metal and related to the overall weight of the material present regarding components (A) to (E).

The amount of filler (D) can be as low as about 3 wt.-%, or as low as about 25 wt.-%, or as low as about 50 wt.-% with respect to the cured composition.

The amount of filler (D) can be as high as about 90 wt.-%, or as high as about 80 wt.-%, or as high as about 75 wt.-% with respect to the cured composition.

Optional component (E) can be present up to an amount of about 25 wt.-%, or up to about 15 wt.-%, or up to about 3 wt.-% with respect to the cured composition.

The dental composition of the invention meets preferably at least one of the following parameters:

The viscosity of carbosilane containing component (A) can be equal or above about 0.1 Pa·s, equal or above about 1 Pa·s, equal or above about 2 Pa·s.

The viscosity of carbosilane containing component (A) usually does not exceed about 40 Pa·s, can be equal or below about 20 Pa·s, or equal or below 5 about Pa·s.

The refractive index of carbosilane containing component (A) usually can be equal or above about 1.510, equal or above about 1.520, equal or above about 1.530.

The refractive index usually does not exceed about 1.600, can be equal or below about 1.580, or equal or below about 1.560.

The opacity of the cured dental composition can be equal or above about 10%, equal or above about 40%, equal or above about 70%.

The opacity usually does not exceed about 92%, can be equal or below about 90%, or equal or below about 88%.

The molecular mass (Mw) of carbosilane containing component (A) can be equal or above about 400, equal or above about 600, or equal or above about 800.

The molecular mass (Mw) usually does not exceed about 10.000, can be equal or below about 5.000, or equal or below about 2000.

The compressive strength can be equal or above about 150 MPa, equal or above about 200 MPa, or equal or above about 250 MPa.

The flexural strength can be equal or above about 50 MPa, preferably equal or above about 65 MPa, more preferably equal or above about 80 MPa.

If not indicated otherwise, the measurements are done at standard temperature and pressure ("STP", i.e. 23° C. and 1023 hPa) according to the methods described below.

The refractive index of carbosilane containing component (A) can be measured with a Kruess AR 4 D device (refractometer according to Abbe's measure principle). The refractive index is measured at 20.0° C. The refractive index is measured at a wavelength of 589 nm.

The viscosity of carbosilane containing component (A) can be measured with a Haake RotoVisco RV1 device (rotor C60/1 for viscosities up to 8000 mPa·s or rotor C20/1 for viscosities above 8000 mPa·s together with stator P61). The viscosity is measured at 23.0° C. between two plane and parallel plates (i.e. stator and rotor). After activation and rectification of the system, the appropriate rotor is installed. Then the rotor is lowered and the distance between stator and rotor is adjusted to 0.052 mm (using Software RheoWin Pro Job Manager Software Version 2.94} for the viscosity measurement. Then the rotor is lifted and the material to be measured is put on the stator (1.0 ml with rotor C60/1 or 0.04 ml with rotor C20/1). Without undue delay, the rotor is lowered back to the preliminary adjusted measuring position. The material to be measured is tempered at 23.0° C. The shear rate for the measurement is adjusted to a value that produced a torque of at least 5000 μNm (therefore normally shear rates of 100, 200, 500, or 1000 s$^{-1}$ were used depending on the viscosity of the material to be measured). The measurement is started and run for 60s. The viscosity values (Pa·s) are recorded 20 s after the start of measurement and the mean value of the recorded values was given as viscosity.

The molecular weight ($M_w$) of carbosilane containing component (A) is determined with GPC. Appropriate methods are know by the expert. In addition the determination of the molecular weight is possible using nuclear magnetic resonance spectroscopy (end-group determination).

The opacity of the cured dental composition is measured by means of specimens with a defined height of 3.6 (+/−0.1) mm and a diameter of 20 (+/−0.1) mm. These are prepared by filling the material to be checked into suitably high rings, evenly and free of bubbles, and curing it chemically by storing it at standard temperature or 50° C. over night between plane, transparent, silicone oil treated glass slides. The opacity is then measured with the colour measuring device "HunterLab LabScan Spectralcolorimeter" of Hunter Lab Associates Laboratory, Inc., USA (Software SpecWare Software Version 1.01) and given by the device in %-values.

The compressive strength and the flexural strength are measured comparably to ISO 9917 respectively according to ISO 4049. For the measurement of the compressive strength 10 specimens (3×3×5 mm) of each material is prepared according to the manufacturer's recommendations and the measurements were carried out comparably to ISO 9917 using an universal testing machine (Zwick Z 010, crosshead speed 4mm/min). The compressive strength is given is MPa. The measurement of the flexural strength is carried out according to ISO 4049 using an universal testing machine (Zwick Z 010, crosshead speed 2 mm/min). The flexural strength is given in MPa.

Carbosilane containing component (A) of the inventive composition can be characterized by formula (A):

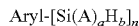

Aryl-[Si(A)$_a$H$_b$]$_n$ (A)

with independently selected from each other
A=(cyclo)aliphatic moiety (C$_1$ to C$_6$, preferably C$_1$), aromatic moiety (C$_6$ to C$_{14}$, preferably phenyl)
Br=bromine atom
C=carbon atom
Cl=chlorine atom
H=hydrogen atom
O=oxygen atom
Si=silicon atom
Aryl=aromatic moiety (C$_6$ to C$_{14}$), preferably benzene, naphthalene, alkoxybenzenes, alkoxy naphthalenes, bisphenol A ethers or bisphenol F ethers
a+b=3
a=0, 1 or 2 (preferably a=2)
b=1, 2 or 3 (preferably b=1)
n=1, 2, 3, 4, 5 or 6 (preferably n=2 to 4).

Carbosilane containing component (A) of the inventive composition thus usually has a comparably high refractive index preferably together with a comparably low viscosity, a comparably high lipophilicity, and a comparably high molecular weight.

Without wishing to be limited to any particular mechanism, it is thought that due to the aromatic moiety within carbosilane containing component (A) the refractive index and the lipophilicity are comparably high which can of some importance for dental materials to achieve appropriate esthetics as well as to avoid staining and/or swelling by uptake of water and/or water soluble dyes (e.g. from coffee, tea, red wine).

Without wishing to be limited to any particular mechanism, it is also thought that due to the comparably high molecular weight of carbosilane containing component (A) and/or different reactivities of Si—H functional moieties Si(A)$_a$H$_b$ within carbosilane containing component (A), the volume shrinkage of derived dental compositions is reduced in comparison to conventional (meth)acrylate composites.

In preferred embodiments carbosilane containing component (A) can be characterized by formulas (I-IV) depending on the molecular structure of carbosilane containing component (A) as well as on the number m of the structural elements {Aryl-[Si(A)$_a$H$_b$]$_n$}$_m$ within carbosilane containing component (A).

In a preferred embodiment carbosilane containing component (A) comprises only one aromatic moiety within the molecule in the structural element {Aryl-[Si(A)$_a$H$_b$]$_n$}$_m$ (i.e. m=1) as well as only one Aryl-Si bond (i.e. n=1) and can be characterized by formula (I), wherein the indices are as defined above:

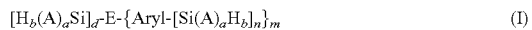

[H$_b$(A)$_a$Si]$_d$-E-{Aryl-[Si(A)$_a$H$_b$]$_n$}$_m$ (I)

wherein
m=1
n=1
d≥1
E=(cyclo)aliphatic moiety (alkadiyl with C$_2$ to C$_{13}$, preferably C$_4$ and C$_6$) wherein C and/or H atoms can be substituted by O, Br, Cl, and Si atoms.
wherein the indices are as defined above.

According to formula (I), the following structural formulas are preferred examples of carbosilane containing component (A):

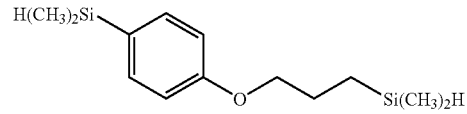

with: A=C$_1$, a=2, b=1, E=C$_4$ with C substituted in part by O and Si, Aryl=phenyl

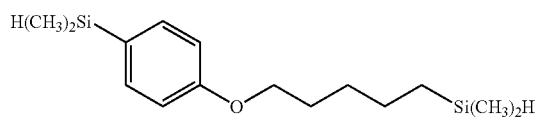

with: A=C$_1$, a=2, b=1, E=C$_6$ with C substituted in part by O and Si, Aryl=phenyl

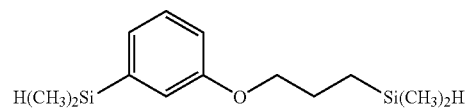

with: A=C$_1$, a=2, b=1, E=C$_4$ with C substituted in part by O and Si, Aryl=phenyl

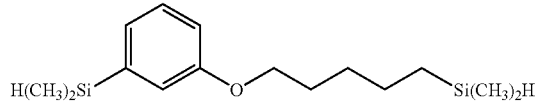

with: A=C$_1$, a=2, b=1, E=C$_6$ with C substituted in part by O and Si, Aryl=phenyl

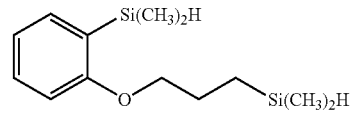

with: A=C$_1$, a=2, b=1, E=C$_4$ with C substituted in part by O and Si, Aryl=phenyl

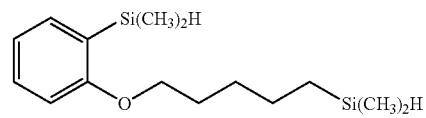

with: A=$C_1$, a=2, b=1, E=$C_6$ with C substituted in part by O and Si, Aryl=phenyl

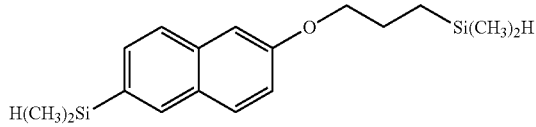

with: A=$C_1$, a=2, b=1, E=$C_4$ with C substituted in part by O and Si, Aryl=naphthyl

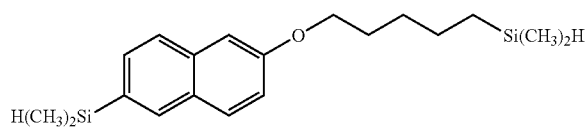

with: A=$C_1$, a=2, b=1, E=$C_6$ with C substituted in part by O and Si, Aryl=naphthyl

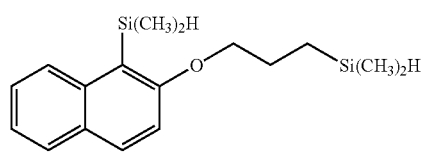

with: A=$C_1$, a=2, b=1, E=$C_4$ with C substituted in part by O and Si, Aryl=naphthyl

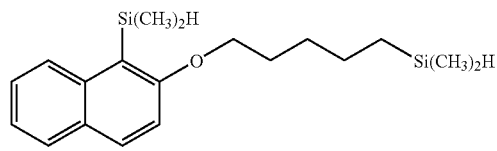

with: A=$C_1$, a=2, b=1, E=$C_6$ with C substituted in part by O and Si, Aryl=naphthyl The following compounds are examples of preferred polyhalogenated precursors of metal organic components (i) used according to scheme (I) for the synthesis of carbosilane containing component (A) via in situ Grignard reaction fulfilling the requirements according to formula (I):

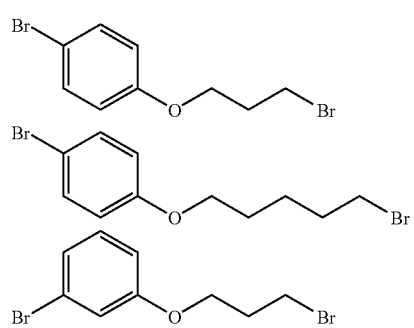

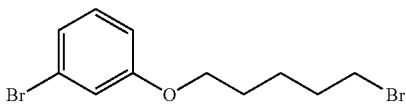

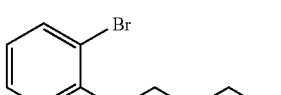

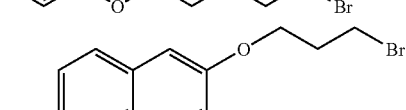

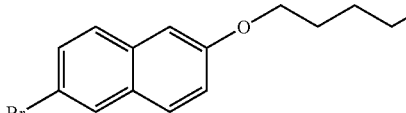

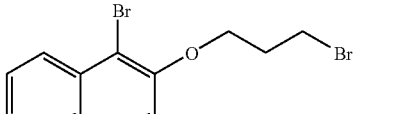

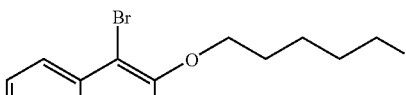

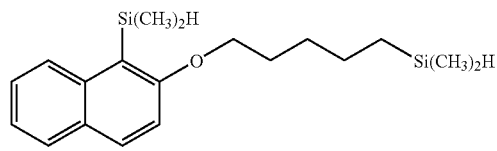

The following compounds are examples of preferred silicon containing components (ii) used according to scheme (I) for the synthesis of carbosilane containing component (A) fulfilling the requirements according to formula (I):

($H_3C$)$_2$SiClH ($H_3C$)($H_5C_6$)SiClH ($H_5C_6$)$_2$SiClH ($H_3C$)SiCl$H_2$ ($H_5C_6$)SiCl$H_2$

ClSi$H_3$

In a further preferred embodiment, carbosilane compound (A) comprises only one aromatic moiety within the molecule in the structural element {Aryl-[Si(A)$_a$H$_b$]$_n$}$_m$ (i.e. m=1) as well as more than one Aryl-Si bond (i.e. n≧2) and can be characterized by formula (II), wherein the indices are as defined above:

$${Aryl-[Si(A)_aH_b]_n}_m \qquad (II)$$

with, independently selected from each other, m=1 n=2, 3, 4, 5 or 6 (preferably 2 and 3)

wherein the indices are as defined above.

According to formula (II), the following structural formulas are preferred examples of carbosilane containing component (A):

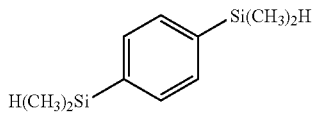

with: A=C$_1$, a=2, b=1, n=2, Aryl=phenyl

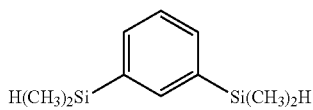

with: A=C$_1$, a=2, b=1, n=2, Aryl=phenyl

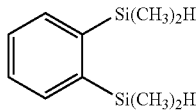

with: A=C$_1$, a=2, b=1, n=2, Aryl=phenyl

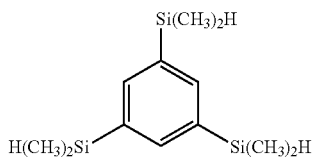

with: A=C$_1$, a=2, b=1, n=3, Aryl=phenyl

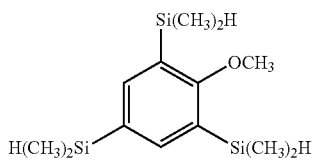

with: A=C$_1$, a=2, b=1, n=3, Aryl=phenyl

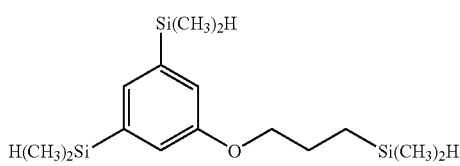

with: A=C$_1$, a=2, b=1, n=2, Aryl=phenyl

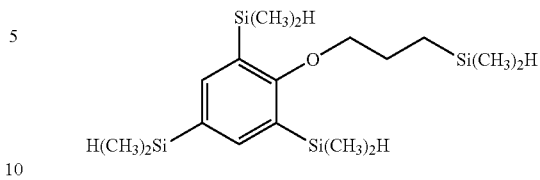

with: A=C$_1$, a=2, b=1, n=3, Aryl=phenyl

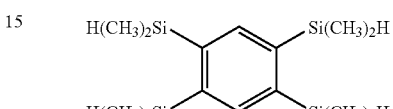

with: A=C$_1$, a=2, b=1, n=4, Aryl=phenyl

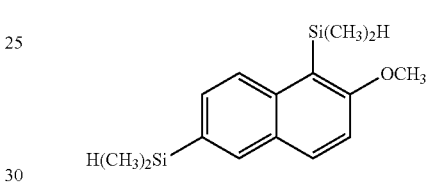

with: A=C$_1$, a=2, b=1, n=2, Aryl=naphthyl

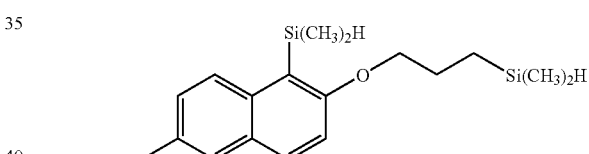

with: A=C$_1$, a=2, b=1, n=2, Aryl=naphthyl

The following compounds are examples of preferred polyhalogenated precursors of metal organic components (i) used according to scheme (I) for the synthesis of carbosilane containing component (A) via in situ Grignard reaction fulfilling the requirements according to formula (II):

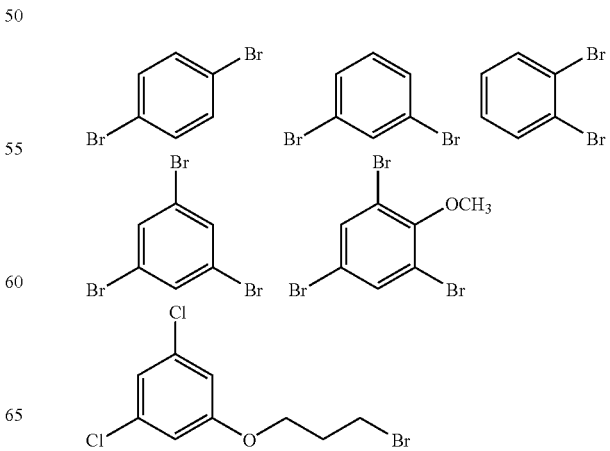

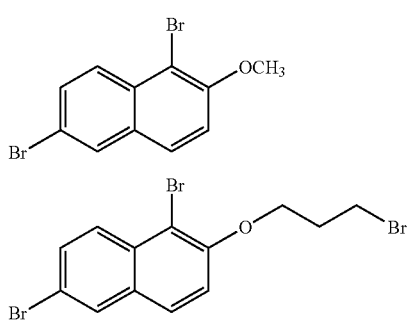

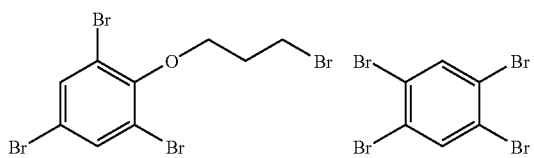

The following compounds are examples of preferred silicon containing components (ii) used according to scheme (I) for the synthesis of carbosilane containing component (A) fulfilling the requirements according to formula (II):

$(H_3C)_2SiClH$ $(H_3C)(H_5C_6)SiClH$ $(H_5C_6)_2SiClH$ $(H_3C)SiClH_2$ $(H_5C_6)SiClH_2$ $ClSiH_3$

In a further preferred embodiment, carbosilane containing component (A) comprises more than one aromatic moiety within the molecule in the structural element $\{Aryl\text{-}[Si(A)_a H_b]_n\}_m$ (i.e. $m \geq 2$) and can be characterized by formula (III), wherein the indices are as defined above:

$$F\text{-}\{Aryl\text{-}[Si(A)_a H_b]_n\}_m \quad (III)$$

with independently selected from each other m=2, 3 or 4 (preferably 2)

n=1, 2, 3, 4, 5 or 6 (preferably 2 to 4)

F=(cyclo)aliphatic moiety (alkadiyl with $C_0$ to $C_{25}$, preferably $C_0$ to $C_9$) wherein C and/or H atoms can also be substituted by O, Br, Cl, and Si atoms.

wherein the indices are as defined above.

According to formula (III) the following structural formulas are preferred examples of carbosilane containing component (A):

with: A=$C_1$, a=2, b=1, m=2, n=1, F=$C_1$ with C substituted by O, Aryl=phenyl

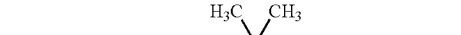

with: A=$C_1$, a=2, b=1, m=2, n=1, F=$C_1$, Aryl=phenyl

![structure]

with: A=$C_1$, a=2, b=1, m=2, n=1,2, F=$C_3$, Aryl=phenyl

![structure]

with: A=$C_1$, a=2, b=1, m=2, n=2, F=$C_3$, Aryl=phenyl

![structure]

with: A=$C_1$, a=2, b=1, m=2, n=2, F=$C_3$, Aryl=phenyl

![structure]

with: A=C₁, a=2, b=1, m=2, n=2, F=C₃, Aryl=phenyl

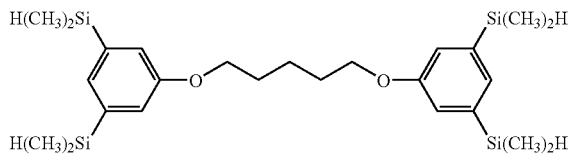

with: A=C₁, a=2, b=1, m=2, n=2, F=C₇ with C substituted in part by O, Aryl=phenyl

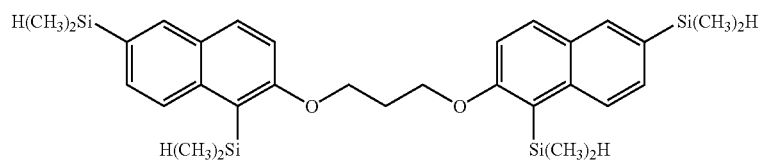

with: A=C₁, a=2, b=1, m=2, n=2, F=C₅ with C substituted in part by O, Aryl=naphthyl

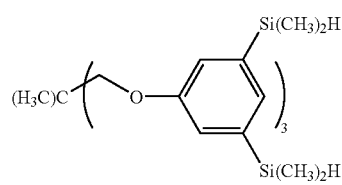

with: A=C₁, a=2, b=1, m=3, n=2, F=C₈ with C substituted in part by O, Aryl=phenyl

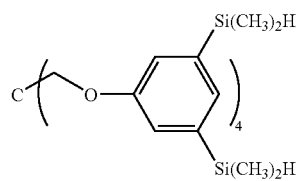

with: A=C₁, a=2, b=1, m=4, n=2, F=C₉ with C substituted in part by O, Aryl=phenyl The following compounds are examples of preferred polyhalogenated precursors of metal organic components (i) used according to scheme (I) for the synthesis of carbosilane containing component (A) via in situ Grignard reaction fulfilling the requirements according to formula (III):

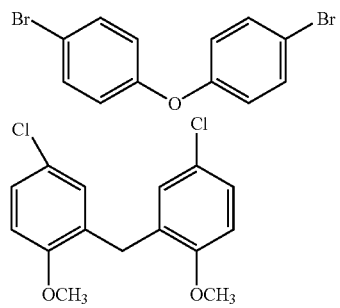

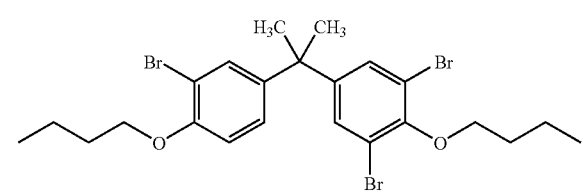

-continued

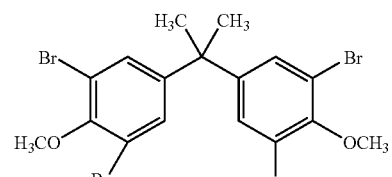

-continued

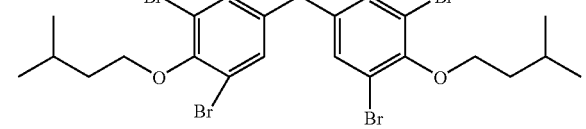

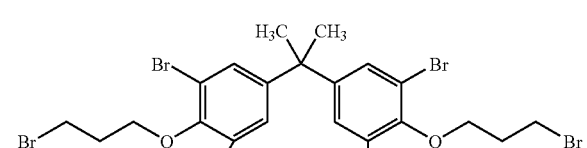

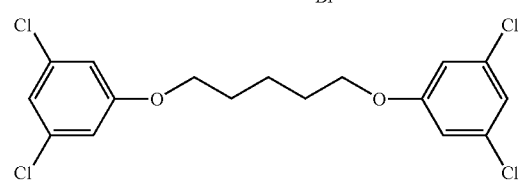

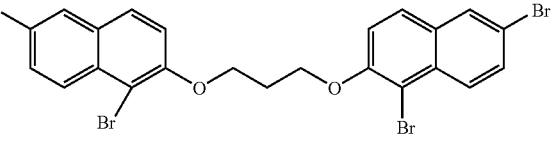

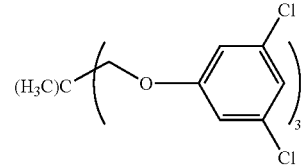

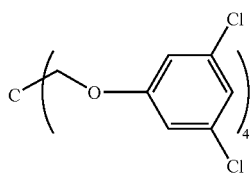

The following compounds are examples of preferred silicon containing components (ii) used according to scheme (I)

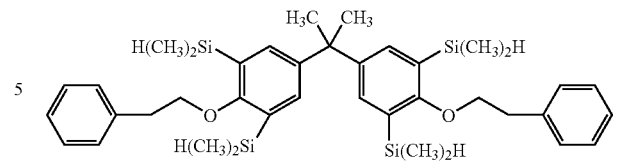

with: A=C$_1$, a=2, b=1, m=2, n=2, G=C$_3$, Aryl=phenyl

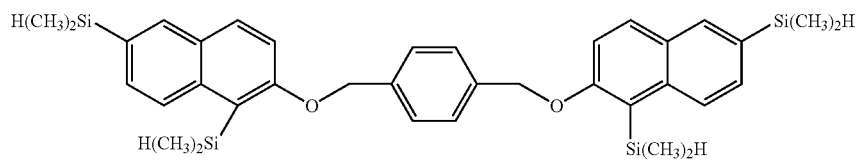

for the synthesis of carbosilane containing component (A) fulfilling the requirements according to formula (III):

(H$_3$C)$_2$SiClH (H$_3$C)(H5C$_6$)SiClH (H$_5$C$_6$)$_2$SiClH (H$_3$C)SiClH$_2$ (H5C$_6$)SiClH$_2$

ClSiH$_3$

In a further preferred embodiment, carbosilane containing component (A) comprises more than one aromatic moiety within the molecule not only in the structural element {Aryl-[Si(A)$_a$H$_b$]$_n$}$_m$ and can be characterized by formula (IV), wherein the indices are as defined above:

with, independently selected from each other, m=2, 3, or 4 (preferably 2)

n=1, 2, 3, 4, 5, or 6 (preferably 2 to 4)

G=(cyclo)aliphatic or aromatic or (cyclo)aliphatic aromatic or aromatic (cyclo)aliphatic moiety (diyl with C$_1$ to C$_{100}$, preferably C$_3$ to C$_{63}$), wherein C and/or H atoms can be substituted by O, Br, Cl, and Si atoms.

wherein the indices are as defined above.

According to formula (IV) the following structural formulas are preferred examples of carbosilane containing component (A):

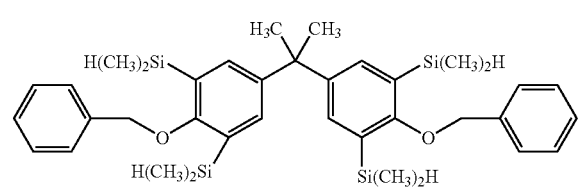

with: A=C$_1$, a=2, b=1, m=2, n=2, G=C$_3$, Aryl=phenyl with: A=C$_1$, a=2, b=1, m=2, n=2, G=C$_{10}$ with C substituted in part by O, Aryl=naphthyl The following compounds are examples of preferred polyhalogenated precursors of metal organic components (i) used according to scheme (I) for the synthesis of carbosilane containing component (A) via in situ Grignard reaction fulfilling the requirements according to formula (IV):

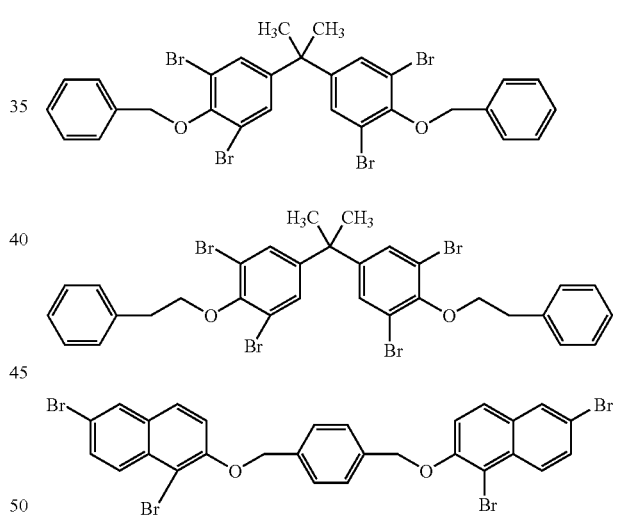

The following compounds are preferred examples of silicon containing components (ii) used according to scheme (I) for the synthesis of carbosilane containing component (A) fulfilling the requirements according to formula (IV):

(H$_3$C)$_2$SiClH (H$_3$C)(H$_5$C$_6$)SiClH (H$_5$C$_6$)$_2$SiClH (H$_3$C)SiClH$_2$ (H$_5$C$_6$)SiClH$_2$

ClSiH$_3$

In a more detailed embodiment of formula (IV) carbosilane containing component (A) can be represented by formula (IVa), wherein the indices are as defined above:

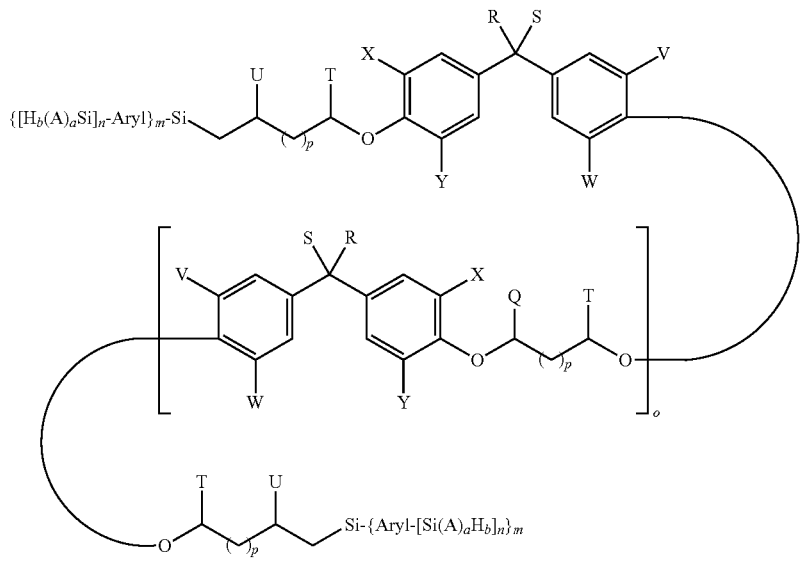

(IVa)

with independently selected from each other
p=0, 1, 2, 3 or 4
o=0, 1, 2, 3, 4 or 5
Q=H, CH$_3$
R, S=H, CH$_3$, phenyl, or C$_{5-9}$ alkadiyl (e.g. R+S=(CH$_2$)$_5$, CH$_2$—CH(CH$_3$)—CH$_2$—CH$_2$—CH$_2$, CH$_2$—CH$_2$—CH(CH3)—CH$_2$—CH$_2$ or CH$_2$—C(CH$_3$)$_2$—CH$_2$—CH(CH$_3$)—CH$_2$)

T, U=H or CH$_3$
V, W, X, Y=H, Br or Cl
wherein the indices are as defined above.

According to formula (IVa) the following structural formulas are preferred examples of carbosilane containing component (A):

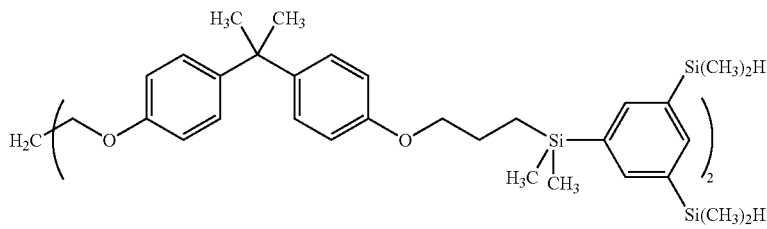

with: A=C$_1$, a=2, b=1, m=2, n=2, G=C$_{49}$ with C substituted in part by O and Si, Aryl=phenyl

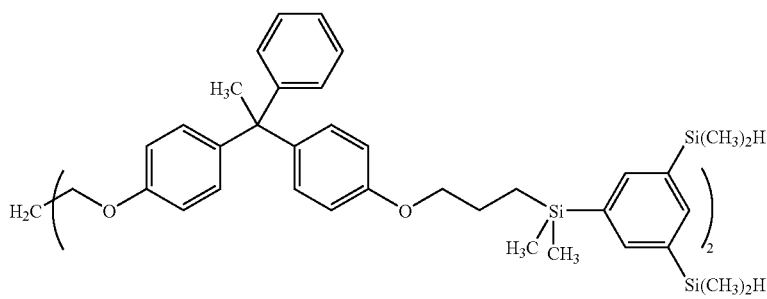

with: A=$C_1$, a=2, b=1, m=2, n=2, G=$C_{59}$ with C substituted in part by O and Si, Aryl=phenyl

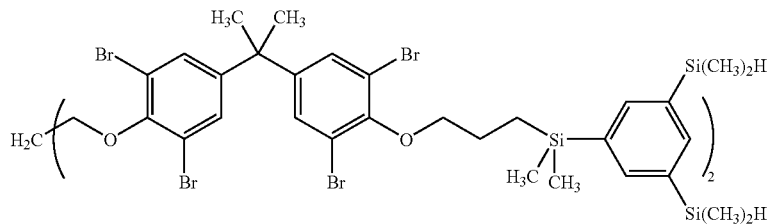

with: A=$C_1$, a=2, b=1, m=2, n=2, G=$C_{57}$ with C substituted in part by Br, O and Si, Aryl=phenyl

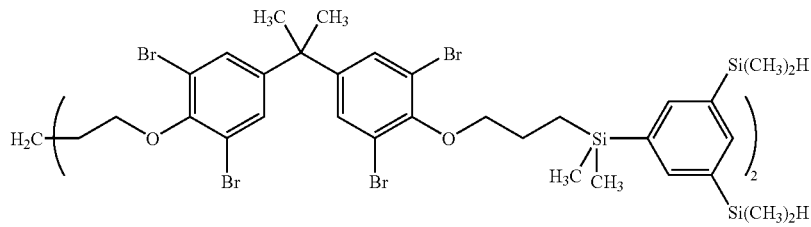

with: A=$C_1$, a=2, b=1, m=2, n=2, G=$C_{63}$ with C substituted in part by Br, O, and Si, Aryl=phenyl In another more detailed embodiment of formula (IVa) for o=0 carbosilane containing component (A) can be represented by formula (IVb), wherein the indices are as defined above:

formula (IVb)

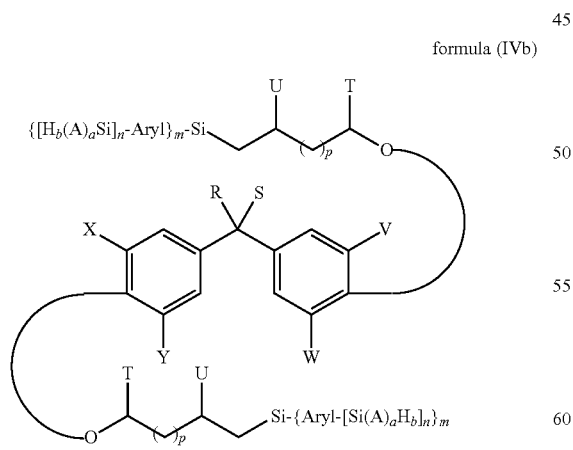

wherein the indices are as defined above.

According to formula (IVb) the following structural formulae are preferred examples of carbosilane containing component (A):

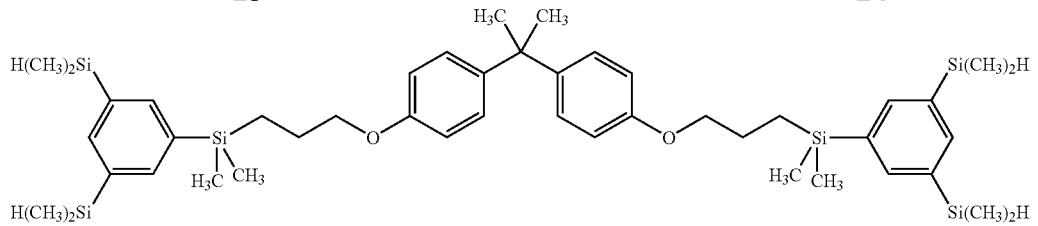

with: A=C$_1$, a=2, b=1, m=2, n=2, G=C$_{29}$ with C substituted in part by O and Si, Aryl=phenyl

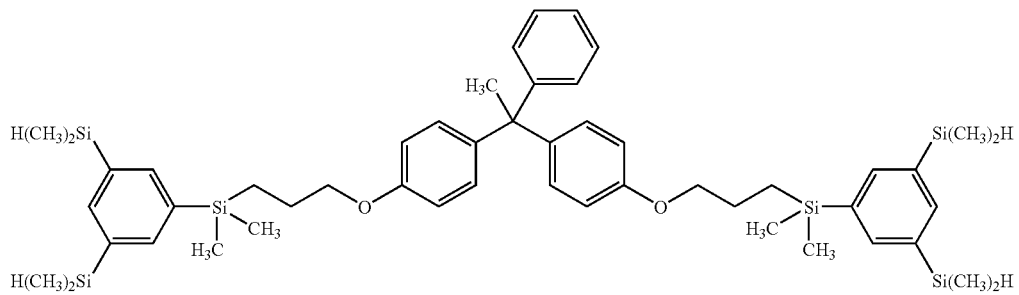

with: A=C$_1$, a=2, b=1, m=2, n=2, G=C$_{34}$ with C substituted in part by O and Si, Aryl=phenyl

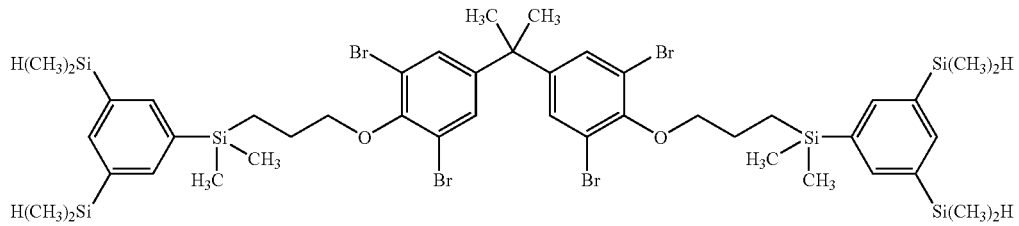

with: A=C$_1$, a=2, b=1, m=2, n=2, G=C$_{33}$ with C substituted in part by Br, O, and Si, Aryl=phenyl

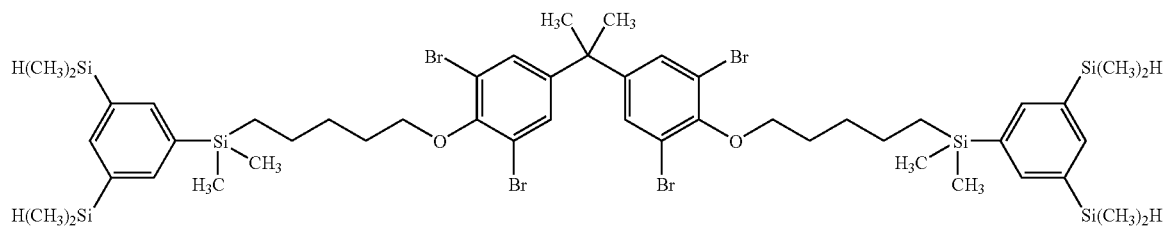

with: A=C$_1$, a=2, b=1, m=2, n=2, G=C$_{37}$ with C substituted in part by Br, O, and Si, Aryl=phenyl The following compounds are examples of preferred poly Si—H functional carbosilane components (iv) used according to scheme (II) for the synthesis of carbosilane containing component (A) fulfilling the requirements according to formulas (IVa and IVb):

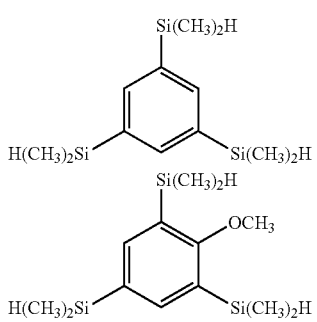

Examples of preferred non-silicon containing diolefinic precursors (v) are:
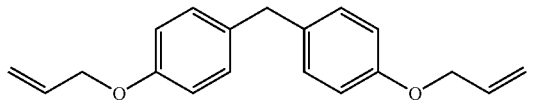
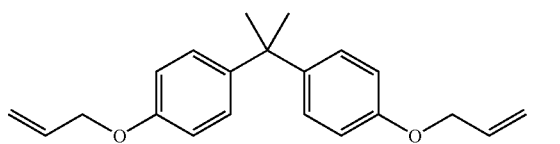
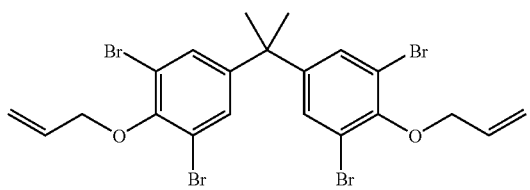
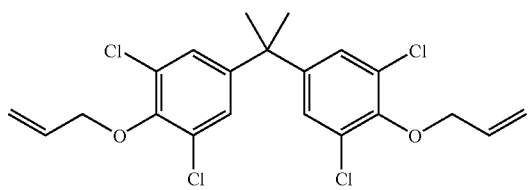
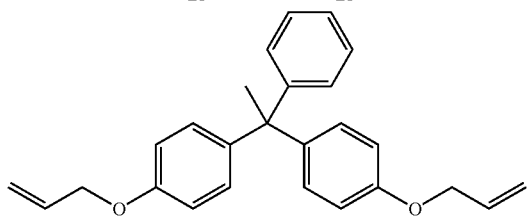
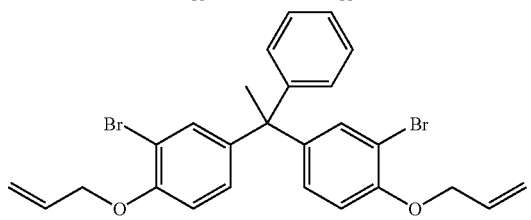
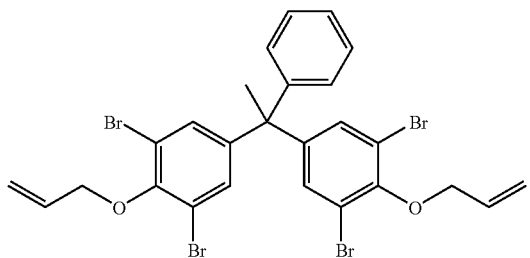
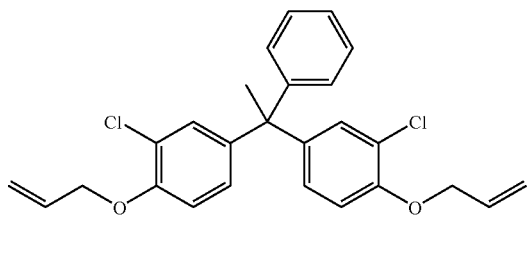
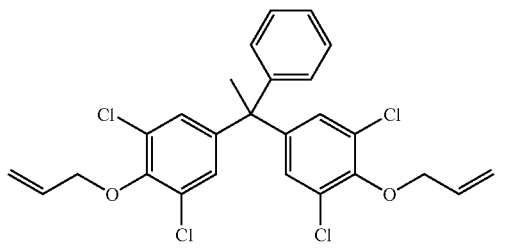
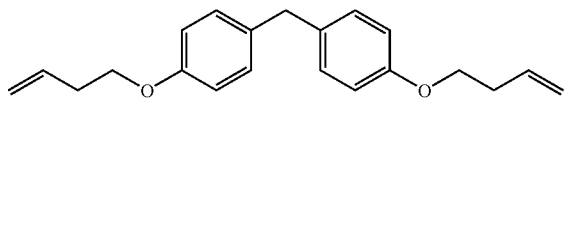
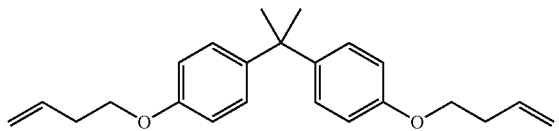
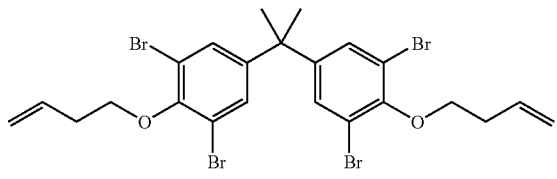
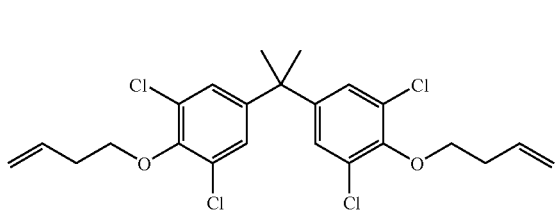
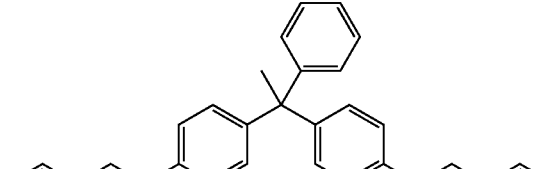
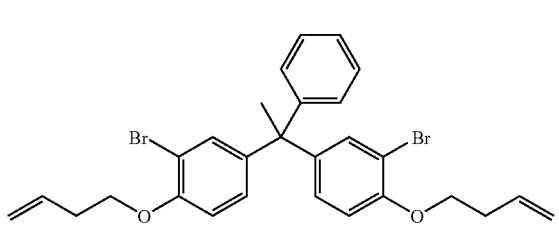
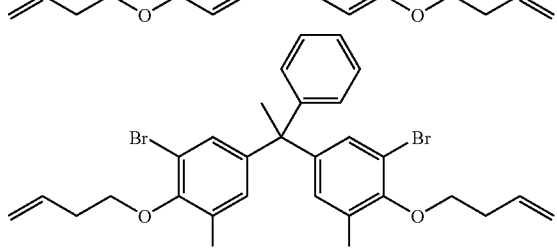

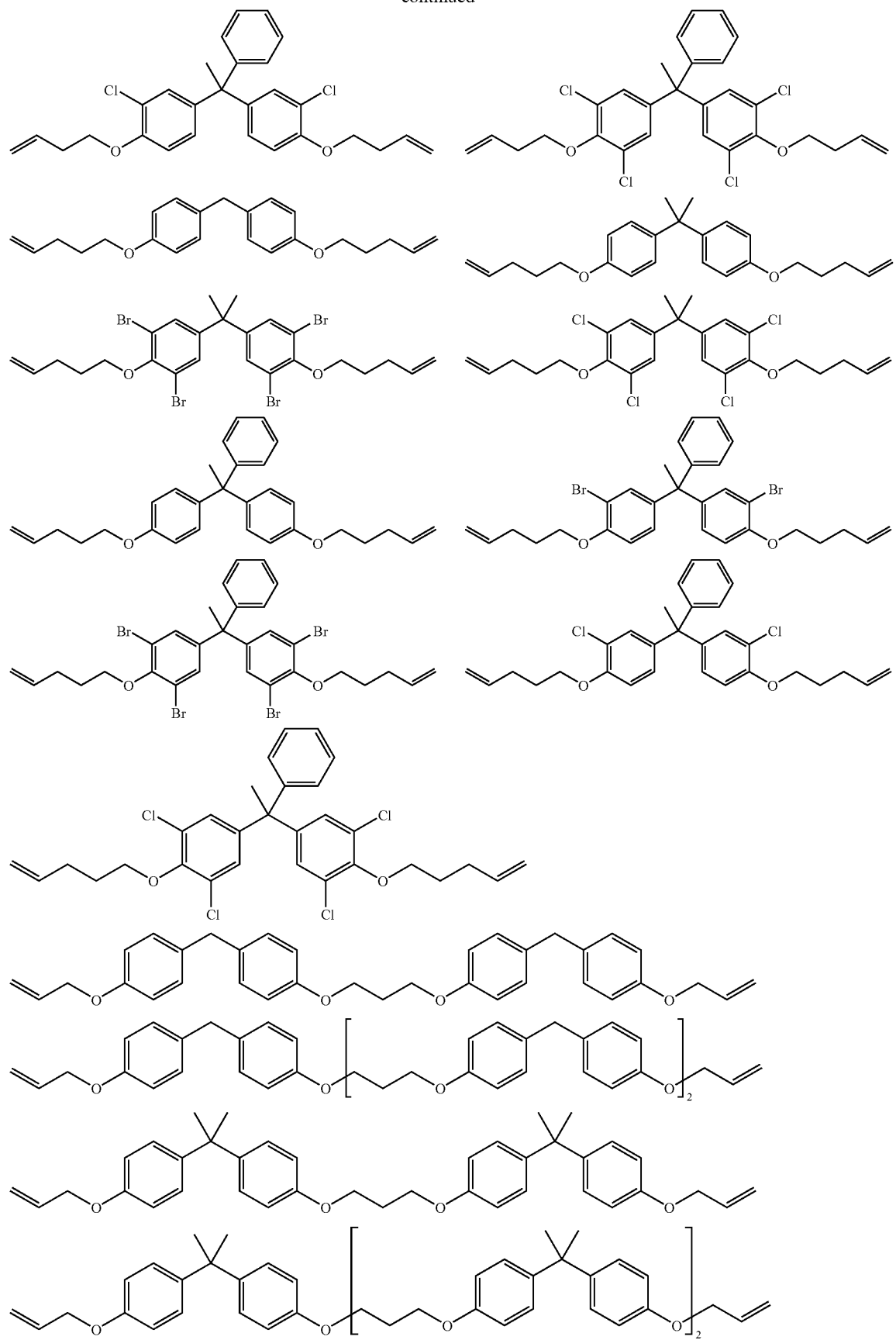

-continued
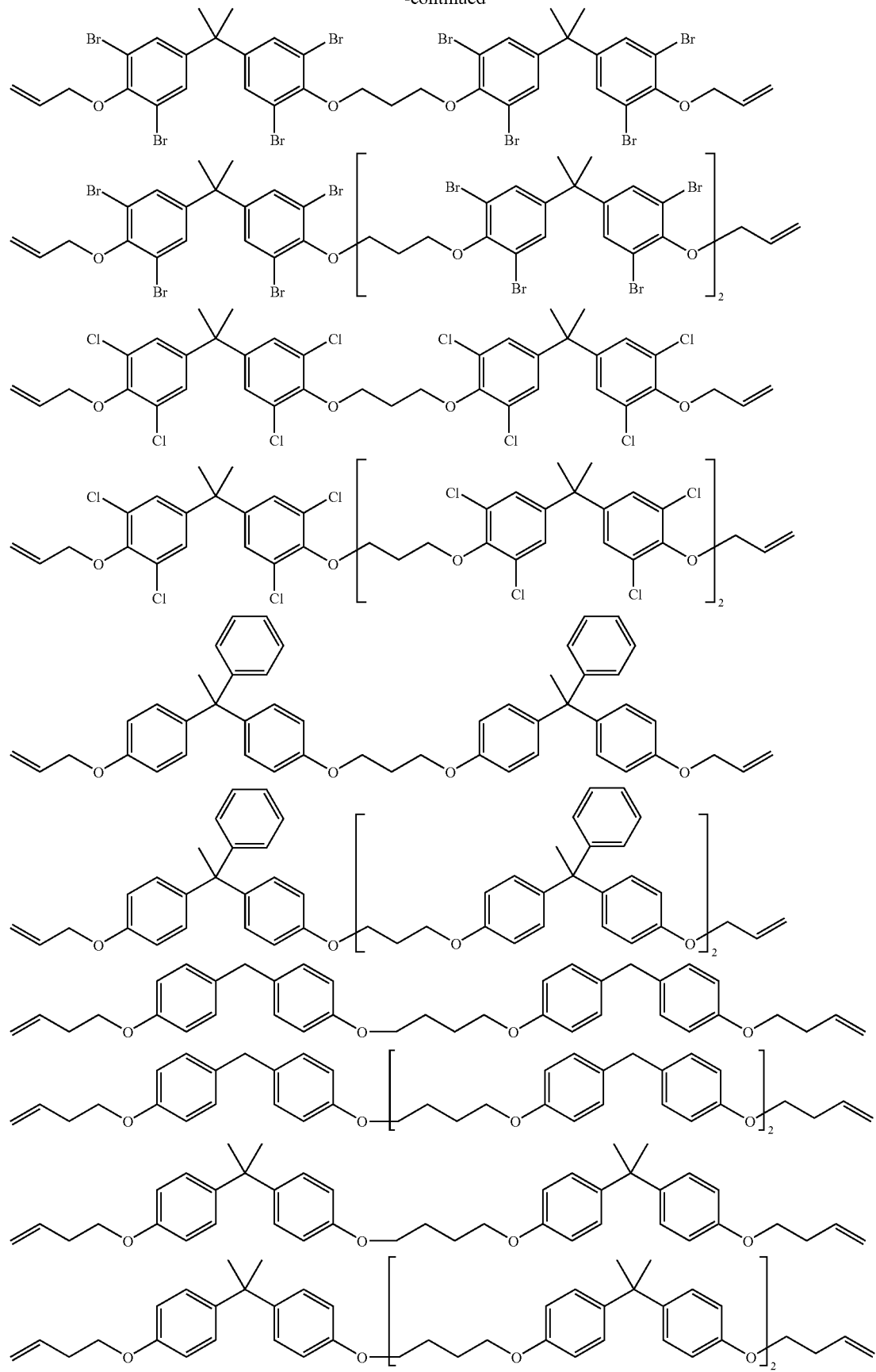

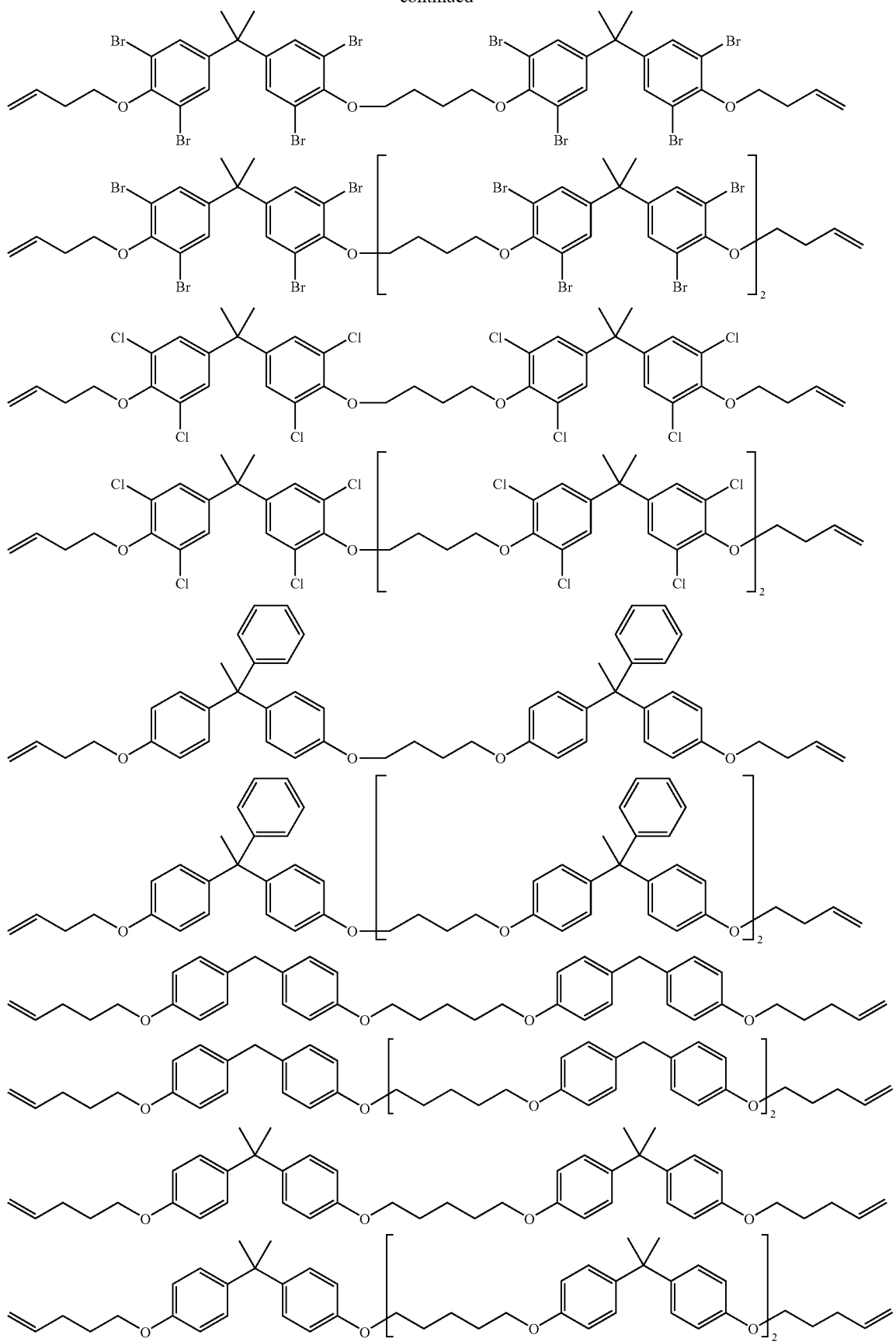

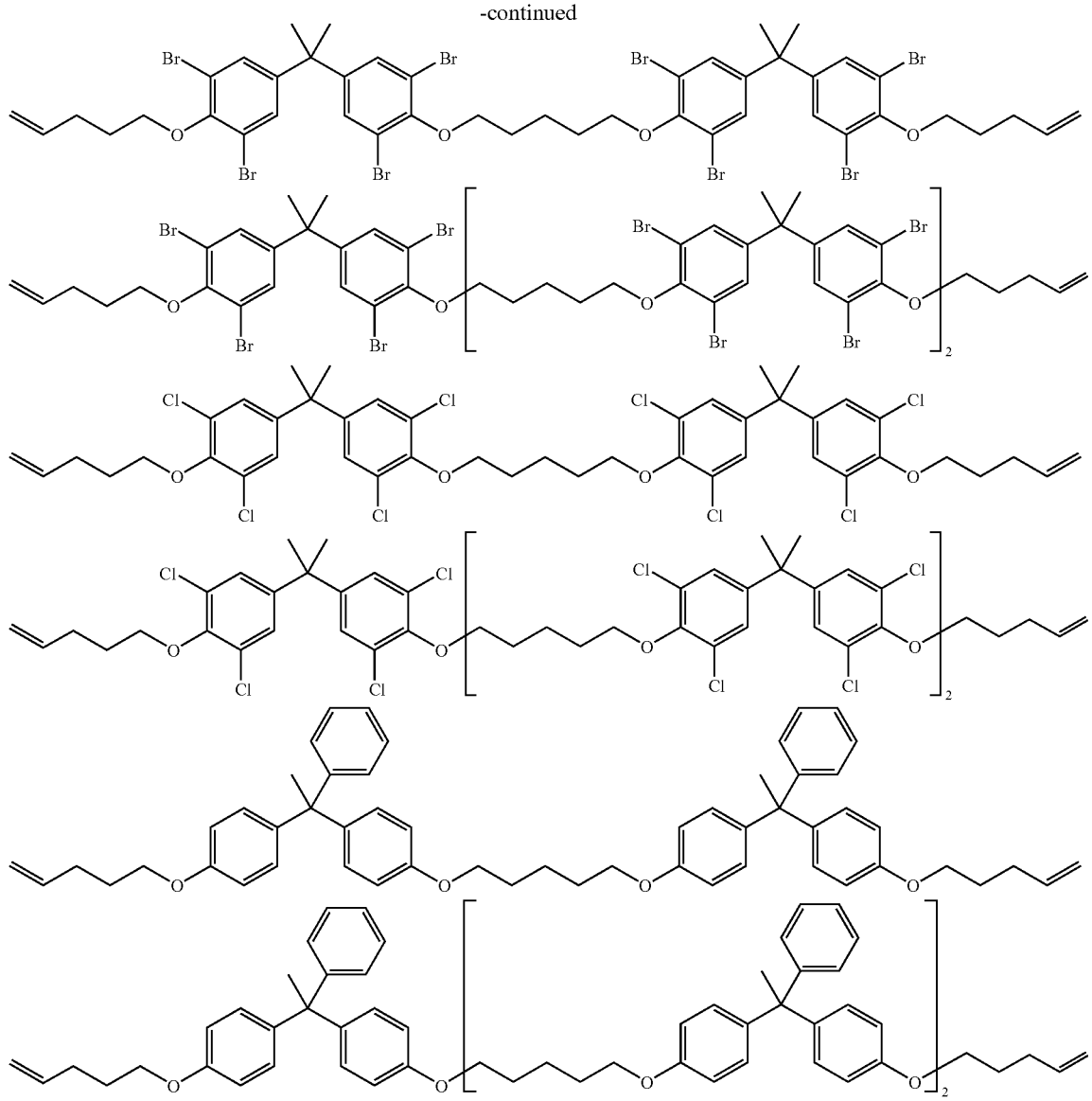

Useful unsaturated components (B1) can react with carbosilane containing component (A) via hydrosilylation reaction. Such unsaturated components (B1) include organopolysiloxane and/or carbosilane derived compounds with olefinic groups as well as other silicon-free compounds bearing olefinic groups. Unsaturated component (B1) is preferably an organopolysiloxane with at least 2 olefinic groups per molecule and/or a carbosilane with at least 2 olefinic groups per molecule and/or a silicon-free compound with at least 2 olefinic groups per molecule.

Useful epoxy components (B2) can react with carbosilane containing component (A) via metal induced cationic ring opening polymerization reaction of epoxies. Such epoxy components (B2) can be organopolysiloxane and/or carbosilane derived compounds with epoxy groups as well as other silicon-free compounds bearing epoxy groups. Epoxy component (B2) is preferably an organopolysiloxane with at least 2 epoxy groups per molecule and/or a carbosilane with at least 2 epoxy groups per molecule and/or a silicon free compound with at least 2 epoxy groups per molecule. Examples of such epoxy components can be found in U.S. Pat. No. 6,245,828 A1, EP 1 368 402 A1 and US 2003035899 A1.

Useful initiators (C) can initiate curing of carbosilane containing component (A) of the composition in the presence of an unsaturated compound (B1) and/or epoxy compound (B2).

Such initiators can be light curing or chemical curing. Both types of initiators are well known to the skilled person in the art.

Representative examples of such initiators include, e.g. complexes of platinum (oxidation states 0 and/or +2), palladium (oxidation states 0 and/or +2), or rhodium (oxidation states 0 and/or +1), as described e.g. within Marciniec, B., Comprehensive Handbook on Hydrosilylation, p8ff., Pergamon Press, Oxford, 1992 or e.g. in U.S. Pat. Nos. 5,145,886, 6,046,250, 6,376,569.

Initiator (C) is preferably a platinum complex which was prepared from hexachloroplatinum acid by reduction with tetramethyldivinyidisiloxane. These compounds are known. Other platinum compounds which can accelerate addition cross-linking, are also suitable. Examples of suitable Platinum-siloxane complexes are described e.g. in U.S. Pat. Nos. 3,715,334, 3,775,352 and 3,814,730. The platinum catalyst is preferably used in quantities of 0.00005 to 0.5 wt.-%, particularly 0.0002 to 0.2 wt.-%, each calculated as elemental platinum and related to the overall weight of the material present regarding components (A) to (E).

To control the reactivity, it may be desirable to add an inhibitor which prevents premature cross-linking to elastomers. Such inhibitors are known and described, e.g. in U.S. Pat. No. 3,933,880. Examples of such include acetylenic unsaturated alcohols such as 3-Methyl-1-butyne-3-ol, 1-Ethynylcyclohexane-1-ol, 3,5-Dimethyl-1-hexyne-3-ol and 3-Methyl-1-pentyne-3-ol. Examples of inhibitors based on vinyl siloxane include 1,1,3,3-Tetramethyl-1,3-divinyl siloxane and poly-, oligo- and disiloxane-containing vinyl groups.

The composition of the present invention may also include filler (D), preferably inorganic fillers like quartz, ground glasses, silica gels as well as pyrogenic silicic acids and precipitation silicic acids or their granules. X-ray-opaque fillers are also preferably used, at least partially. These can, for example, be X-ray-opaque glasses, i.e. glasses which, for example, contain strontium, barium or lanthanum (e.g. according to U.S. Pat. No. 3,971,754) Some of the fillers may contain an X-ray-opaque additive, such as yttrium trifluoride, strontium hexafluorozirconate or fluorides of the rare earth metals (e.g. according to EP 0 238 025 A1). For better incorporation into the polymer matrix, it may be advantageous to hydrophobize the inorganic fillers. Typical hydrophobization agents include silanes, e.g. (5-Hexenyl)trimethoxysilane or [2-(3-Cyclohexenyl)-ethyl]trimethoxysilane. The fillers preferably have an average grain size <20 µm, particularly <5 µm and more particularly <2 µm and an upper grain limit of 150 µm, particularly 70 µm and more particularly 25 µm. Such fillers can be present in amounts of from about 3 to about 90 weight percent, especially about 25 to about 80 or about 50 to about 75 wt.-% of the composition.

Non-reinforcing fillers may also be used in the invention such as quartz, cristobalite, calcium silicate, diatomaceous earth, zirconium silicate, montmorillonite such as bentonite, zeolite, including moleculer sieves such as sodium aluminium silicate, metal oxide powder such as aluminium or zinc oxide or their mixed oxides, barium sulphate, calcium carbonate, plaster, glass and plastic powder.

Suitable fillers also include reinforcing fillers such as e.g. pyrogenic or precipitated silicic acid and silica aluminium mixed oxides. The above mentioned fillers can be hydrophobized, for example by treatment with organosilanes or siloxanes or by the etherification of hydroxyl groups to alkoxy groups. One type of filler or also a mixture of at least two fillers can be used.

A combination of reinforcing and non-reinforcing fillers is particularly preferred. In this respect, the quantity of reinforcing fillers can vary from about 1 to about 10 wt.-%, and in particular, from about 2 to about 5 wt.-%.

The difference in the named overall ranges, i.e. about 2 to about 89 wt.-% is accounted for by non-reinforcing fillers.

Pyrogenically-prepared highly-disperse, silicic acids which have preferably been hydrophobized by surface treatment are preferred as reinforcing fillers. The surface treatment can be carried out, e.g. with dimethyldichlorosilane, hexamethyldisilazane, tetramethylcyclotetrasiloxane or polymethylsiloxane.

Particularly preferred non-reinforcing fillers are quartzes, cristobalites, calcium carbonate and sodium aluminium silicates which can be surface-treated. The surface treatment can generally be carried out with the same methods as described in the case of the strengthening fillers.

Optionally additives (E) like stabilizers, modifiers, dyes, pigments, thixotropic agents, flow improvers, or thinning agents, polymeric thickeners, surfactants, and diluting agent(s) can be added alone or in admixture.

The above described carbosilane containing component (A) can be used as monomer in dental compositions that are curable preferably via hydrosilylation reaction and/or metal induced cationic ring opening polymerization of epoxies.

The dental composition of the invention can be used as dental filling materials, crown and bridge materials, veneer materials, inlays or onlays.

Carbosilane containing component (A) can also be used for preparing a dental material in a process comprising the steps of
a) providing a dental composition comprising carbosilane containing component (A);
b) applying the dental composition to a surface;
c) curing the dental composition.

The surface is usually a surface of a tooth, a crown or a bridge.

The dental compositions of the invention can be provided as a 1 part mixture or as a 2 part mixture. This usually depends on the initiator used. If the initiator is light curing, the dental composition can be provided as a 1 part mixture, if the initiator is redox curing, the dental composition should be provided as a 2 part mixture.

Therefore, the invention also relates to a kit of parts, comprising a base part (I) and a catalyst part (II), wherein the base part (I) comprises carbosilane containing component (A), unsaturated component (B1), and/or epoxy component (B2), and filler (D), and the catalyst part (II) comprises initiator (C), and wherein component (E) is present either in the base part or the catalyst part or in the base part and the catalyst part.

The dental compositions of the invention is usually packaged in a container or cartridge, preferably in a dental compule. Examples of such computes are described in U.S. Pat. Nos. 5,322,440 A1or 4,391,590 or 5,165,890.

The invention also relates to a method of producing a curable dental composition comprising the steps:
a) providing components (A), (B1), and/or (B2), (C), optionally (D) and optionally (E) as described above;
b) mixing the components of step a),
wherein compound (A) is obtainable via Grignard reaction or in situ Grignard reaction or is obtainable via hydrosilylation reaction.

The Grignard reaction or in situ Grignard reaction comprises reacting (poly)organometallic functional component (i) or (poly)halogenated precursor and silicon containing component (ii) as describe above.

The hydrosilylation reaction comprises reacting poly Si—H functional carbosilane component (iv) and non silicon containing diolefinic precursor (v) as describe above.

EXAMPLES

The invention is hereinafter described by examples. The examples are for illustrative purpose only and not intended to limit the invention.

The compounds listed in table 1 were prepared according to the references listed above and their refractive index and viscosity measured.

TABLE 1

| Examples of Compounds | Refractive Index | Viscosity [mPa*s] | Molecular Weight [g/mol] |
|---|---|---|---|
| Reference Compound 1: 1,3,5,7-Tetramethyl-1,3,5,7-tetravinyl-cyclotetrasiloxane | 1.434 | 400 | 344.7 |
| Reference Compound 2: 1,3,5,7-Tetramethyl-cyclotetrasiloxane | 1.387 | 200 | 240.5 |
| Example Compound 1: 1,5-Bis[3,5-bis(dimethylsilyl)-phenoxy]-pentane | 1.531 | 320 | 489.0 |
| Example Compound 2: 2,2-Bis{3,5-bis(dimethylsilyl)-4-[3-(dimethylsilyl)propyloxy]-phenyl}-propane | 1.527 | 1660 | 661.4 |

Dental compositions containing carbosilane compounds according to the invention as well as dental compositions containing state of the art reference compounds were prepared and their opacity measured.

TABLE 2

| Amounts in %-Weight | Examples of Dental Compositions | | |
|---|---|---|---|
| | 1 | 2 | 3 |
| Reference Compound 1 | 20.3 | 28.3 | 33.9 |
| Reference Compound 2 | 30.5 | | |
| Example Compound 1 | | 22.6 | |
| Example Compound 2 | | | 17.0 |
| (1,3,5,7-Tetramethyl-1,3,5,7-tetravinyl)platinum(0) | 1.4 | 1.4 | 1.4 |
| Quartz, mean particle size <2 μm | 30.4 | 30.4 | 30.4 |
| Hydrophobized Highly-Disperse Silicic Acid | 17.4 | 17.3 | 17.3 |
| Opacity [%] | 95.6 | 82.2 | 75.9 |
| Exact Height of Specimen [mm] | (3.6) | (3.6) | (3.6) |

The invention claimed is:

1. A dental composition comprising:
   a) a carbosilane containing component comprising:
      at least one Si-Aryl bond,
      at least one silicon atom,
      at least two Si—H functional moieties, and
      no Si-Oxygen bond;
   b) an unsaturated component, and/or an epoxy component; and
   c) an initiator
   wherein
   the carbosilane containing component comprises a compound represented by the following Formula (I):

$[H_b(A)_aSi]_d$-E-$\{Aryl\text{-}[Si(A)_aH_b]_n\}_m$ (I)

wherein, in Formula (I), independently selected from each other,
   A is an aliphatic or cycloaliphatic moiety ($C_1$ to $C_6$) or aromatic moiety ($C_6$ to $C_{14}$);
   H is a hydrogen atom;
   Si is a silicon atom;
   Aryl is an aromatic moiety ($C_6$ to $C_{14}$);
   a+b is 3;
   a is 0, 1, or 2;
   b is 1, 2, or 3;
   m is 1;
   n is 1;
   d is 1; and
   E is a (cyclo)aliphatic moiety (alkadiyl with $C_2$ to $C_{13}$) wherein C and/or H atoms can be substituted by O, Br, Cl and Si atoms; and/or the carbosilane containing component comprises a compound represented by the following Formula (II):

$\{Aryl\text{-}[Si(A)_aH_b]_n\}_m$ (II)

wherein, in Formula (II), independently selected from each other,
   A is an aliphatic or cycloaliphatic moiety ($C_1$ to $C_6$) or aromatic moiety ($C_6$ to $C_{14}$);
   H is a hydrogen atom;
   Si is a silicon atom;
   Aryl is an aromatic moiety ($C_6$ to $C_{14}$);
   a+b is 3;
   a is 0, 1, or 2;
   b is 1, 2, or 3;
   m is 1; and
   n is 3, 4, 5 or 6; and/or the carbosilane containing component comprises a compound represented by the following Formula (III):

F-$\{Aryl\text{-}[Si(A)_aH_b]_n\}_m$ (III)

wherein, independently selected from each other,
   A is an aliphatic or cycloaliphatic moiety ($C_1$ to $C_6$) or aromatic moiety ($C_6$ to $C_{14}$);
   H is a hydrogen atom;
   Si is a silicon atom;
   Aryl is an aromatic moiety ($C_6$ to $C_{14}$);
   a+b is 3;
   a is 0, 1, or 2;
   b is 1, 2, or 3;
   m is 3 or 4;
   n is 1, 2, 3, 4, 5, or 6; and
   F is a (cyclo)aliphatic moiety ($C_1$ to $C_{25}$) wherein C and/or H atoms can be substituted by O, Br, Cl, and Si atoms; and/or the carbosilane containing component comprises a compound represented by the following Formula (IV):

G-$\{Aryl\text{-}[Si(A)_aH_b]_n\}_m$ (IV)

wherein, independently selected from each other,
   A is an aliphatic or cycloaliphatic moiety ($C_1$ to $C_6$) or aromatic moiety ($C_6$ to $C_{14}$);
   H is a hydrogen atom;
   Si is a silicon atom;
   Aryl is an aromatic moiety ($C_6$ to $C_{14}$);
   a+b is 3;
   a is 0, 1, or 2;
   b is 1, 2, or 3;
   m is 2, 3, 4;
   n is 1, 2, 3, 4, 5, or 6; and
   G is a (cyclo)aliphatic or aromatic or (cyclo)aliphatic aromatic or aromatic (cyclo)aliphatic moiety ($C_1$ to $C_{100}$) wherein C and/or H atoms can be substituted by O, Br, Cl, and Si atoms; and/or the carbosilane containing component comprises a compound represented by one of formulas (IVa) or (IVb):

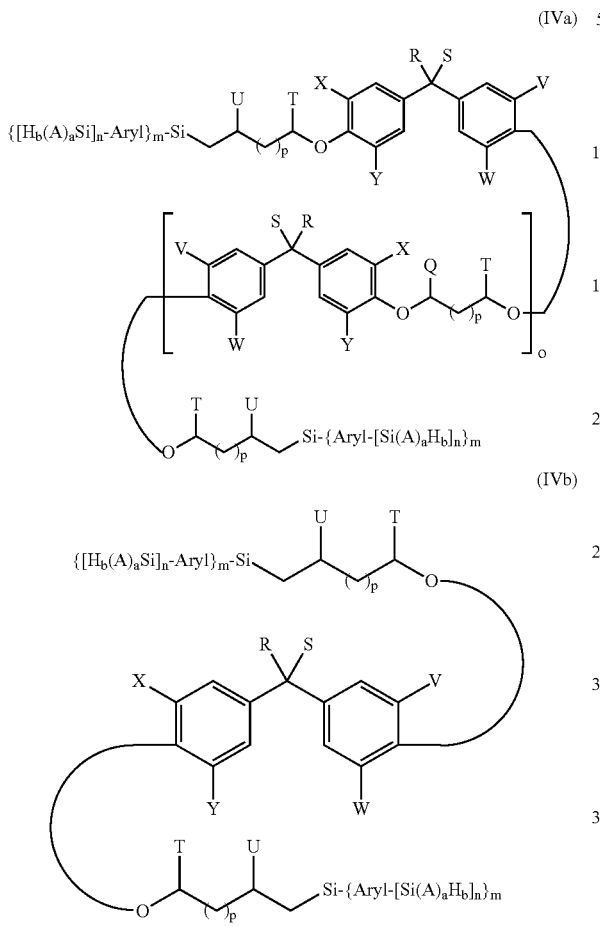

wherein, in each of Formula (IVa) and Formula (IVb), independently selected from each other,
A is an aliphatic or cycloaliphatic moiety ($C_1$ to $C_6$) or aromatic moiety ($C_6$ to $C_{14}$);
H is a hydrogen atom;
Si is a silicon atom;
Aryl is an aromatic moiety ($C_6$ to $C_{14}$);
a+b is 3;
a is 0, 1, or 2;
b is 1, 2, or 3;
n is 1, 2, 3, 4, 5, or 6,
m is 1, 2, 3, or 4;
p is 0, 1, 2, 3, or 4;
o is 0, 1, 2, 3, 4 or 5;
Q is H or $CH_3$;
each of R and S is H, $CH_3$, phenyl or alkadiyl $C_5$ to $C_8$;
each of T and U is H or $CH_3$; and
each of V, W, X and Y is H, Br or Cl.

2. The dental composition of claim 1, further comprising a filler.

3. The dental composition of claim 2, further comprising an additive selected from modifiers, dyes, pigments, thixotropic agents, flow improvers, polymeric thickeners, surfactants, odorous substances, diluting agent(s) and flavourings.

4. The dental composition of claim 1, wherein the carbosilane containing component has a refractive index equal to or above about 1.510.

5. The dental composition of claim 1, wherein the carbosilane containing component has a viscosity equal to or above about 0.1 Pa·s.

6. The dental composition of claim 1, wherein the carbosilane containing component has a molecular mass equal to or above about 400.

7. The dental composition of claim 1, wherein the opacity of the cured composition is equal to or above about 10%.

8. The dental composition of claim 1, wherein the compressive strength of the cured composition is equal to or above about 150 MPa.

9. The dental composition of claim 1, wherein the flexural strength of the cured composition is equal to or above about 50 MPa.

10. The dental composition of claim 3, wherein the carbosilane containing component is present in an amount of at least 1% by weight;
the unsaturated component, and/or an epoxy component is present in an amount of at least 1% by weight;
the initiator comprising a metal, is present in an amount of at least 0.00005% by weight, calculated as elemental metal;
the filler is present in an amount of at least 3% by weight; and
the additive is present in an amount of less than 25% by weight, with respect to the whole composition.

11. The dental composition of claim 1 wherein the carbosilane containing component is selected from $H(CH_3)_2Si$—⟨phenyl⟩—O—(CH₂)₃—$Si(CH_3)_2H$ $H(CH_3)_2Si$—⟨phenyl with $Si(CH_3)_2H$⟩—$Si(CH_3)_2H$ $H(CH_3)_2Si$, $H(CH_3)_2Si$—⟨bisphenol A structure with $Si(CH_3)_2H$ groups⟩—$Si(CH_3)_2H$, $Si(CH_3)_2H$

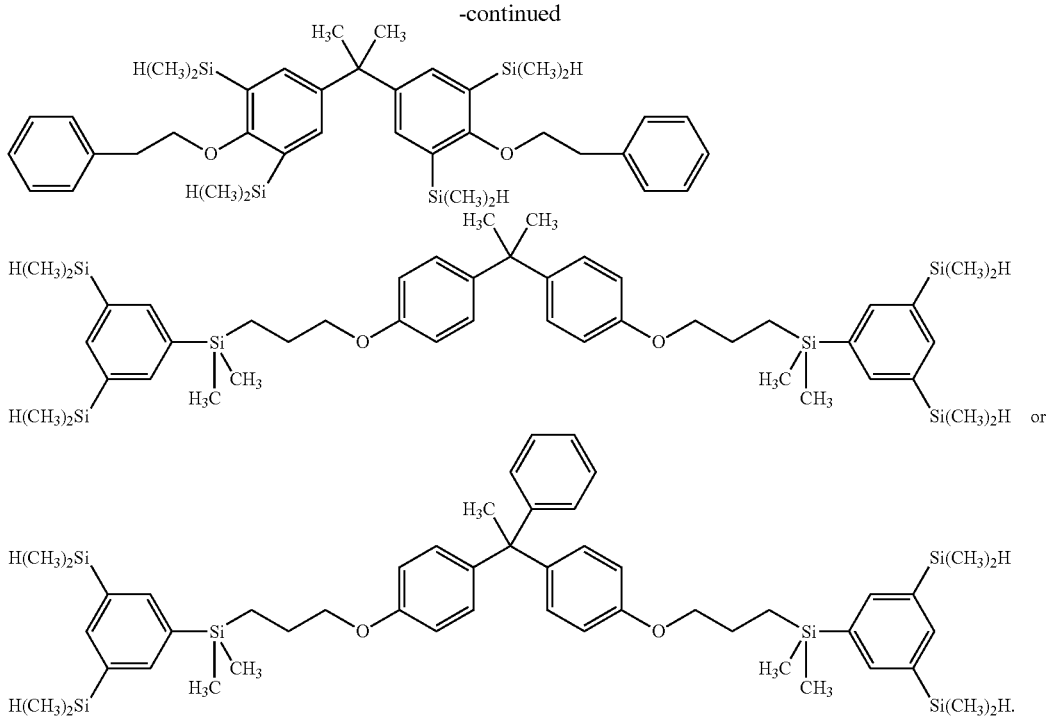

12. The dental composition of claim 1, wherein the unsaturated component is selected from organopolysiloxane and/or carbosilane derived compounds with olefinic groups as well as other silicon free compounds bearing olefinic groups.

13. The dental composition of claim 1, wherein the epoxy component is selected from organopolysiloxane and/or carbosilane derived compounds with epoxy groups as well as other silicon free compounds bearing epoxy groups.

14. The dental composition of claim 1, wherein the initiator comprises a light curing initiator or a chemical curing initiator or a combination of both.

15. The dental composition of claim 1, wherein the filler comprises reinforcing or non-reinforcing fillers or a combination of both.

16. A container or cartridge filled with the dental composition of claim 1.

17. A kit of parts comprising a base part and a catalyst part, wherein the base part comprises the carbosilane containing component of claim 1, an unsaturated component and/or epoxy component, and a filler, and the catalyst part comprises an initiator and wherein an additive component is present either in the base part or the catalyst part or in the base part and the catalyst part.

18. A method of producing the curable dental composition of claim 1 comprising the steps;
   a) providing the carbosilane containing component of claim 1, an unsaturated and/or epoxy component, and an initiator; and
   b) mixing the components of step a),
      wherein the carbosilane containing component is obtained via a Grignard reaction, or a hydrosilylation reaction.

19. The method of claim 18, wherein the carbosilane containing component is obtained from a hydrosilylation reaction comprises reacting
   a poly Si—H functional carbosilane component and
   a non silicon containing diolefinic precursor.

20. A dental material selected from dental filling materials, crown or bridge materials, veneer materials, inlays and onlays, wherein the material comprises the dental composition of claim 1.

21. A method for preparing a dental material comprising the steps of:
   a) providing the dental composition of claim 1;
   b) applying the dental composition to a surface; and
   c) curing the dental composition.

* * * * *

UNITED STATES PATENT AND TRADEMARK OFFICE
CERTIFICATE OF CORRECTION

| | |
|---|---|
| PATENT NO. | : 8,003,711 B2 |
| APPLICATION NO. | : 11/572056 |
| DATED | : August 23, 2011 |
| INVENTOR(S) | : Peter Bissinger |

It is certified that error appears in the above-identified patent and that said Letters Patent is hereby corrected as shown below:

<u>First Page, Col. 2 (Other Publications)</u>
| | |
|---|---|
| Line 1 | Delete "Phenenyl" and insert -- Phenyl --, therefor. |
| Line 8 | Delete "Hydosilylation," and insert -- Hydrosilylation, --, therefor. |
| Lines 13-15 | After "1992." delete "Tarbell, D., S., Wilson, J., W., The Rearrangement of 4-Crotyloxy-3,5-Dichlorobenzoic Acid, J. Am. Chem. Soc. 1942, 64(5), 1066-1070." and insert as a new entry. |

<u>Column 1</u>
| | |
|---|---|
| Line 48 | Delete "siiloxane" and insert -- siloxane --, therefor. |
| Line 57 | Delete "visclosity." and insert -- viscosity. --, therefor. |

<u>Column 3</u>
| | |
|---|---|
| Line 66 | Delete "prepartion" and insert -- preparation --, therefor. |

<u>Column 5</u>
| | |
|---|---|
| Line 8 (Approx.) | After "composition" insert -- . --. |
| Line 49 | Delete "Pa·s," and insert -- Pa*s, --, therefor. |
| Line 49 | Delete "Pa·s," and insert -- Pa*s, --, therefor. |
| Line 50 | Delete "Pa·s." and insert -- Pa*s. --, therefor. |
| Line 52 | Delete "Pa·s." and insert -- Pa*s. --, therefor. |
| Line 53 | Delete "Pa·s." and insert -- Pa*s. --, therefor. |
| Line 53 | Delete "Pa·s." and insert -- Pa*s. --, therefor. |

<u>Column 6</u>
| | |
|---|---|
| Line 20 | Delete "mPa·s" and insert -- mPa*s --, therefor. |
| Line 21 | Delete "mPa·s" and insert -- mPa*s --, therefor. |
| Line 27 | Delete "2.94}" and insert -- 2.94) --, therefor. |
| Line 37 | Delete "(Pa·s)" and insert -- (Pa*s) --, therefor. |
| Line 42 | Delete "know" and insert -- known --, therefor. |

Signed and Sealed this
Twenty-second Day of November, 2011

David J. Kappos
*Director of the United States Patent and Trademark Office*

Column 7
Line 22 (Approx.)    Delete "5or" and insert -- 5 or --, therefor.
Line 64              Delete "(alkadiyl" and insert -- (alkanediyl --, therefor.
Line 66              Delete "atoms." and insert -- atoms, --, therefor.

Column 13
Line 50 (Approx.)    Delete "(alkadiyl" and insert -- (alkanediyl --, therefor.
Line 52 (Approx.)    Delete "atoms." and insert -- atoms, --, therefor.

Column 17
Line 28 (Approx.)    Delete "($H_3C$)(H5$C_6$)SiClH" and insert -- ($H_3C$)($H_5C_6$)SiClH --, therefor.
Line 32 (Approx.)    Delete "(H5$C_6$)SiCl$H_2$" and insert -- ($H_5C_6$)SiCl$H_2$ --, therefor.
Line 49 (Approx.)    Delete "(diyl" and insert -- (alkanediyl --, therefor.
Line 51 (Approx.)    Delete "atoms." and insert -- atoms, --, therefor.

Column 19
Line 30              Delete "alkadiyl" and insert -- alkanediyl --, therefor.
Line 32              Delete "C($CH_3$) $_2$" and insert -- C($CH_3$)$_2$ --, therefor.

Column 34
Line 65              Delete "tetramethyldivinyidisiloxane." and insert
                     --tetramethyldivinyldisiloxane. --, therefor.

Column 35
Line 25              After "3,971,754)" insert -- . --.
Line 32              Delete "[2-(3-Cyclohexenyl) -ethyl]trimethoxysilane." and insert
                     -- [2-(3-Cyclohexenyl)-ethyl]trimethoxysilane. --, therefor.
Line 42              Delete "moleculer" and insert -- molecular --, therefor.
Line 63              Delete "hexamethyldisilazane," and insert -- hexamethyldisilane, --, therefor.

Column 36
Lines 39-40          Delete "compule." and insert -- computes. --, therefor.
Line 41              Delete "A1or" and insert -- A1 or --, therefor.

Column 37
Line 65              In Claim 1, delete "(alkadiyl" and insert -- (alkanediyl --, therefor.

Column 40
Line 4               In Claim 1, delete "6," and insert -- 6; --, therefor.
Line 9 (Approx.)     In Claim 1, delete "alkadiyl" and insert -- alkanediyl --, therefor.
Line 17 (Approx.)    In Claim 3, delete "agent(s)" and insert -- agents, --, therefor.
Line 20 (Approx.)    In Claim 4, after "above" delete "about".
Lines 22-23          In Claim 5, delete "above about 0.1 Pa·s." and insert -- above 0.1 Pa*s. --,
                     therefor.

CERTIFICATE OF CORRECTION (continued)
U.S. Pat. No. 8,003,711 B2

| | |
|---|---|
| Line 26 (Approx.) | In Claim 6, after "above" delete "about". |
| Line 28 (Approx.) | In Claim 7, after "above" delete "about". |
| Line 31 (Approx.) | In Claim 8, after "above" delete "about". |
| Line 33 (Approx.) | In Claim 9, after "above" delete "about". |
| Line 40 (Approx.) | In Claim 10, delete "initiator" and insert -- initiator, --, therefor. |